(12) United States Patent
McNaughton et al.

(10) Patent No.: US 10,195,547 B2
(45) Date of Patent: Feb. 5, 2019

(54) METHOD AND SYSTEM FOR BUOYANT SEPARATION

(71) Applicant: Akadeum Life Sciences, LLC, Ann Arbor, MI (US)

(72) Inventors: Brandon H. McNaughton, Ann Arbor, MI (US); John G. Younger, Ann Arbor, MI (US); Leo J. Ostruszka, Ann Arbor, MI (US)

(73) Assignee: Akadeum Life Sciences, Inc., Ann Arbor, MI (US)

( * ) Notice: Subject to any disclaimer, the term of this patent is extended or adjusted under 35 U.S.C. 154(b) by 259 days.

(21) Appl. No.: 14/969,446

(22) Filed: Dec. 15, 2015

(65) Prior Publication Data

US 2016/0167061 A1  Jun. 16, 2016

Related U.S. Application Data

(60) Provisional application No. 62/092,019, filed on Dec. 15, 2014, provisional application No. 62/189,518, filed on Jul. 7, 2015.

(51) Int. Cl.
*B01L 3/00* (2006.01)
*B01D 21/26* (2006.01)
*G01N 33/49* (2006.01)

(52) U.S. Cl.
CPC .......... *B01D 21/262* (2013.01); *B01L 3/5021* (2013.01); *B01L 2200/026* (2013.01); *B01L 2400/0616* (2013.01); *G01N 33/491* (2013.01)

(58) Field of Classification Search
CPC ................ B01D 21/262; B01L 3/5021; B01L 2200/026; B01L 2400/0616; G01N 33/491; B04B 7/18

(Continued)

(56) References Cited

U.S. PATENT DOCUMENTS 3,586,064 A * 6/1971 Brown .................... B01L 3/502
141/1
3,920,549 A  11/1975 Gigliello et al.
(Continued)

FOREIGN PATENT DOCUMENTS

DE        3381283    *  4/1990  ............. B01D 33/01
WO   2013096157 A1      6/2013

OTHER PUBLICATIONS

Partial European Search Report for EP Application No. 15870844.6 dated Jul. 10, 2018.

*Primary Examiner* — Walter D. Griffin
*Assistant Examiner* — Shuyi S. Liu
(74) *Attorney, Agent, or Firm* — Jeffrey Schox

(57) ABSTRACT

A method and system for buoyant separation of a target constituent of a sample, the method comprising: at a process chamber, combining a volume of substrates having a first density with the sample, thereby producing a population of target-bound complexes comprising the target constituent bound to at least a portion of the volume of substrates; within the process chamber, physically separating the population of target-bound complexes from the sample based upon interaction between the volume of substrates and an applied force; aggregating the population of target-bound complexes at a collection region of the process chamber; extracting the population of target-bound complexes from the process chamber; and processing the target constituent from the population of target-bound complexes for further analysis.

8 Claims, 20 Drawing Sheets

(58) Field of Classification Search
USPC .............................................. 494/37, 56, 67
See application file for complete search history.

(56) References Cited

U.S. PATENT DOCUMENTS

| | | | |
|---|---|---|---|
| 4,086,060 A | | 4/1978 | Hermann |
| 4,464,254 A | * | 8/1984 | Dojki .................... B01L 3/5021 |
| | | | 210/136 |
| 4,487,700 A | | 12/1984 | Kanter |
| 4,845,025 A | | 7/1989 | Lary et al. |
| 5,266,199 A | * | 11/1993 | Tsukagoshi .......... G01N 33/491 |
| | | | 210/514 |
| 5,339,830 A | * | 8/1994 | Blake, III .......... G01N 33/4905 |
| | | | 422/73 |
| 5,594,164 A | | 1/1997 | Bull |
| 5,853,600 A | | 12/1998 | McNeal et al. |
| 6,036,940 A | | 3/2000 | Ju et al. |
| 6,506,167 B1 | * | 1/2003 | Ishimito ................ B01L 3/5021 |
| | | | 600/577 |
| 6,652,136 B2 | | 11/2003 | Marziali |
| 8,048,320 B2 | | 11/2011 | Leach et al. |
| 8,835,186 B2 | | 9/2014 | Jablonski et al. |
| 2004/0023222 A1 | | 2/2004 | Russell et al. |
| 2004/0166029 A1 | | 8/2004 | Losada et al. |
| 2005/0059163 A1 | | 3/2005 | Dastane et al. |
| 2007/0075016 A1 | | 4/2007 | Leach |
| 2010/0285606 A1 | | 11/2010 | Phillips et al. |
| 2014/0161688 A1 | | 6/2014 | Campton et al. |
| 2015/0011013 A1 | * | 1/2015 | Campton ............. B01D 21/262 |
| | | | 436/177 |
| 2015/0219636 A1 | | 8/2015 | Rychak et al. |

\* cited by examiner

CONCAVE

CONVEX

PLANAR

Linear Frustoconical

Curved Frustoconical

Prismatic

Before Separation
After Separation
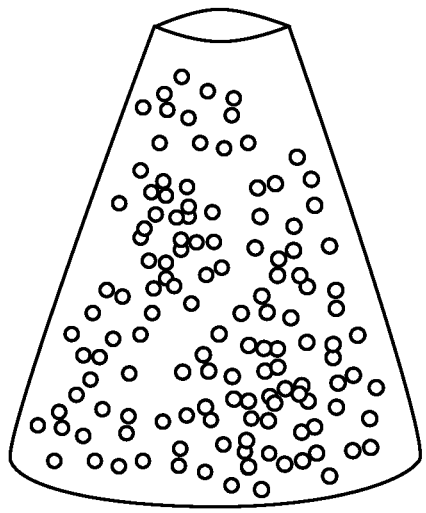
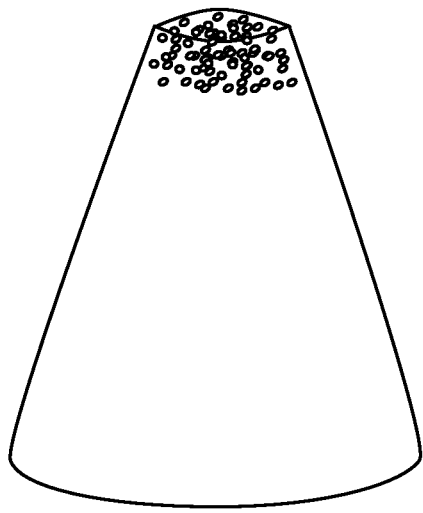
FIGURE 4A
FIGURE 4B
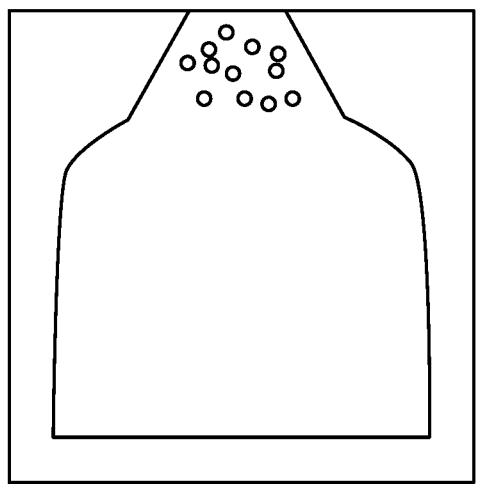
FIGURE 5

Before Contact

Ring

After Contact

Buoyant Particles

Void

Sample Fluid

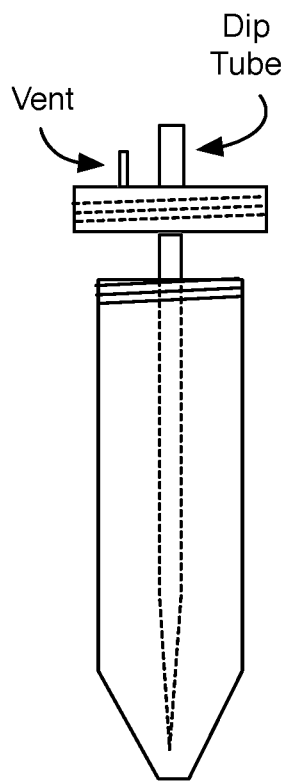
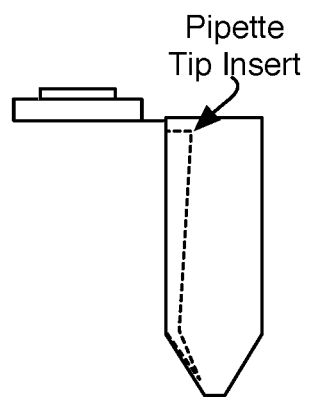
FIGURE 12A
FIGURE 12B
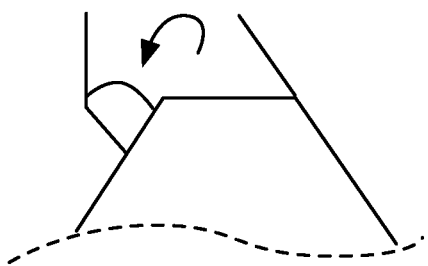
Particle-containing meniscus displaced into sample cup at apex of conical geometry
FIGURE 13

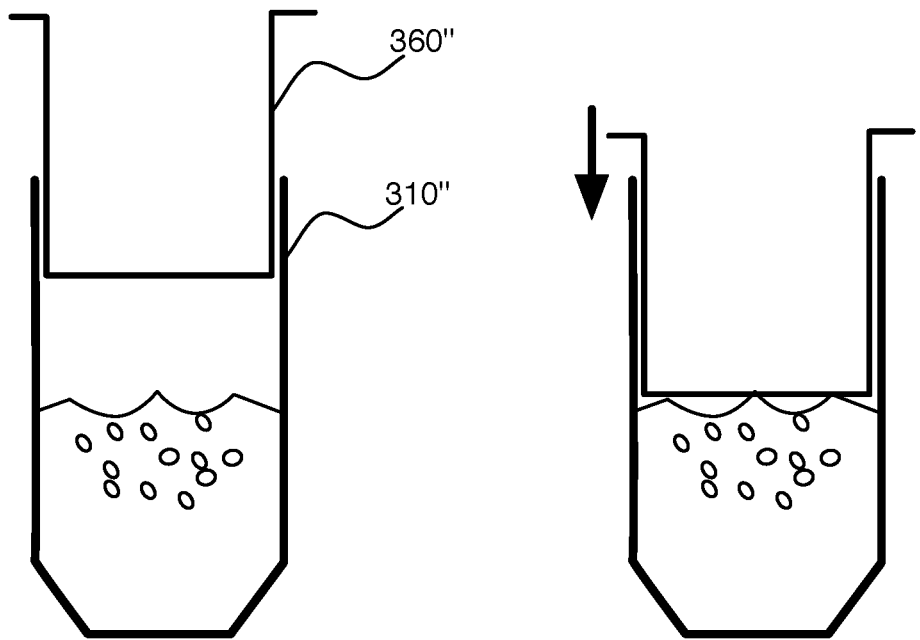
FIGURE 16C
FIGURE 16D
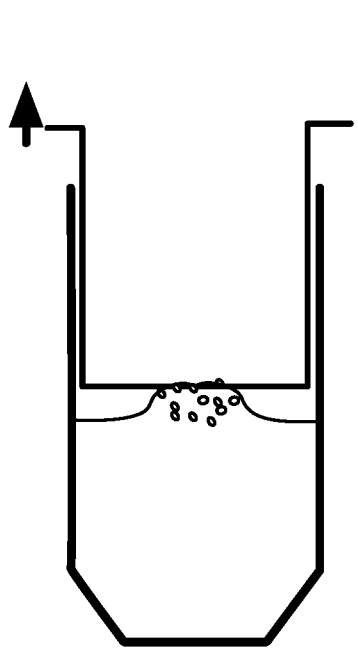
FIGURE 16E
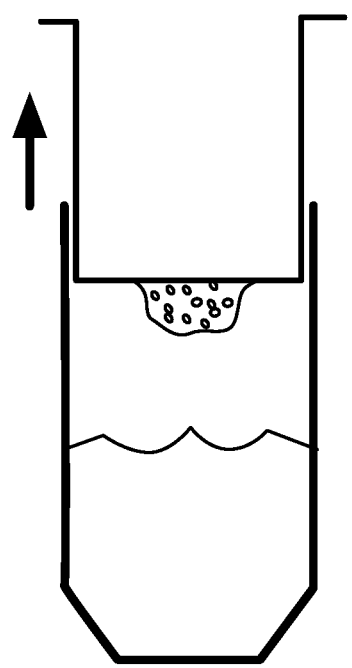
FIGURE 16F

Compression of the bag

METHOD AND SYSTEM FOR BUOYANT SEPARATION

CROSS-REFERENCE TO RELATED APPLICATIONS

This application claims the benefit of U.S. Provisional Application Ser. No. 62/092,019, filed on 15 Dec. 2014 and U.S. Provisional Application Ser. No. 62/189,518 filed on 7 Jul. 2015, which are each incorporated herein in its entirety by this reference.

TECHNICAL FIELD

This invention relates generally to separation methods and systems in the fields of biological sample processing. More specifically, it relates to an improved method and system for buoyant separation of particles in a sample of biological fluid.

BACKGROUND

In research and diagnostic applications, it is often important to be able to isolate one or more types of particles of a sample. Isolation of target components in an efficient and high throughput manner can thus have a significant impact in healthcare applications, biological research, research in the food industry, and medical research. Components for isolation and extraction can include cells, proteins, nucleic acids, lipids, and other particles commonly found in biological fluid, and in one example, efficient isolation of rare cancerous cells (e.g., circulating tumor cells) in a biological sample can be used to detect and/or diagnose cancer for a patient at an early stage where intervention is critical. There are several conventional setups used for particle isolation from samples, implementing techniques derived from one or more of: fluorescence activated sorting, magnetic sorting, filtration, electrophoretic separation, and other methods of separation. However, conventional particle isolation systems are typically inefficient, are not high-throughput, are labor intensive, are prone to user-error, and require large systems, necessitating a significant amount of training, and/or contributing to untrustworthy analyses. Conventional setups are also typically expensive to operate, from time, labor, and cost perspectives, which can provide limits upon the completeness of an analysis performed using such setups.

Thus, there is a need in the biological sample processing field to create an improved method and system for buoyant separation of target components of a sample. This invention provides such an improved method and system.

BRIEF DESCRIPTION OF THE FIGURES

FIGS. 4A and 4B depict a specific example of a process chamber used in an embodiment of a method for buoyant separation of a target constituent of a sample;

FIG. 5 depicts a specific example of a process chamber used in an embodiment of a method for buoyant separation of a target constituent of a sample;

FIGS. 12A and 12B depict examples of process chambers used in a method for buoyant separation of a target constituent of a sample;

FIG. 13 depicts an example of a process chamber for buoyant separation of a target constituent of a sample;

FIGS. 16A-16F depict a second variation of an embodiment of a system for buoyant separation of a target constituent of a sample;

DESCRIPTION OF THE PREFERRED EMBODIMENTS

The following description of preferred embodiments and examples of the invention is not intended to limit the invention to these preferred embodiments and examples, but rather to enable any person skilled in the art to make and use this invention.

1. Method

Figure 1A:
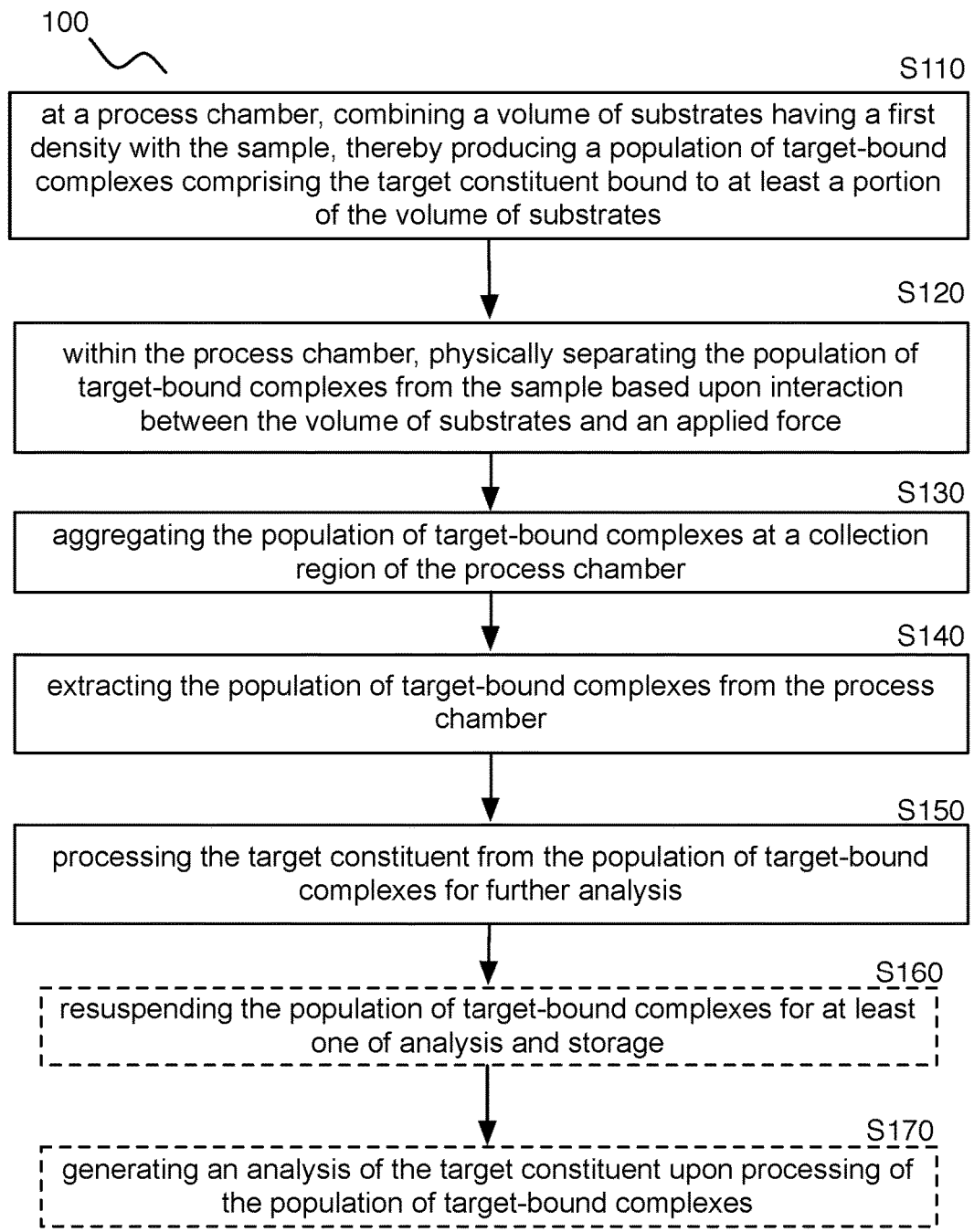
FIGS. 1A and 1B are flowchart schematics of embodiments of a method for buoyant separation of a target constituent of a sample.
Figure 1B:
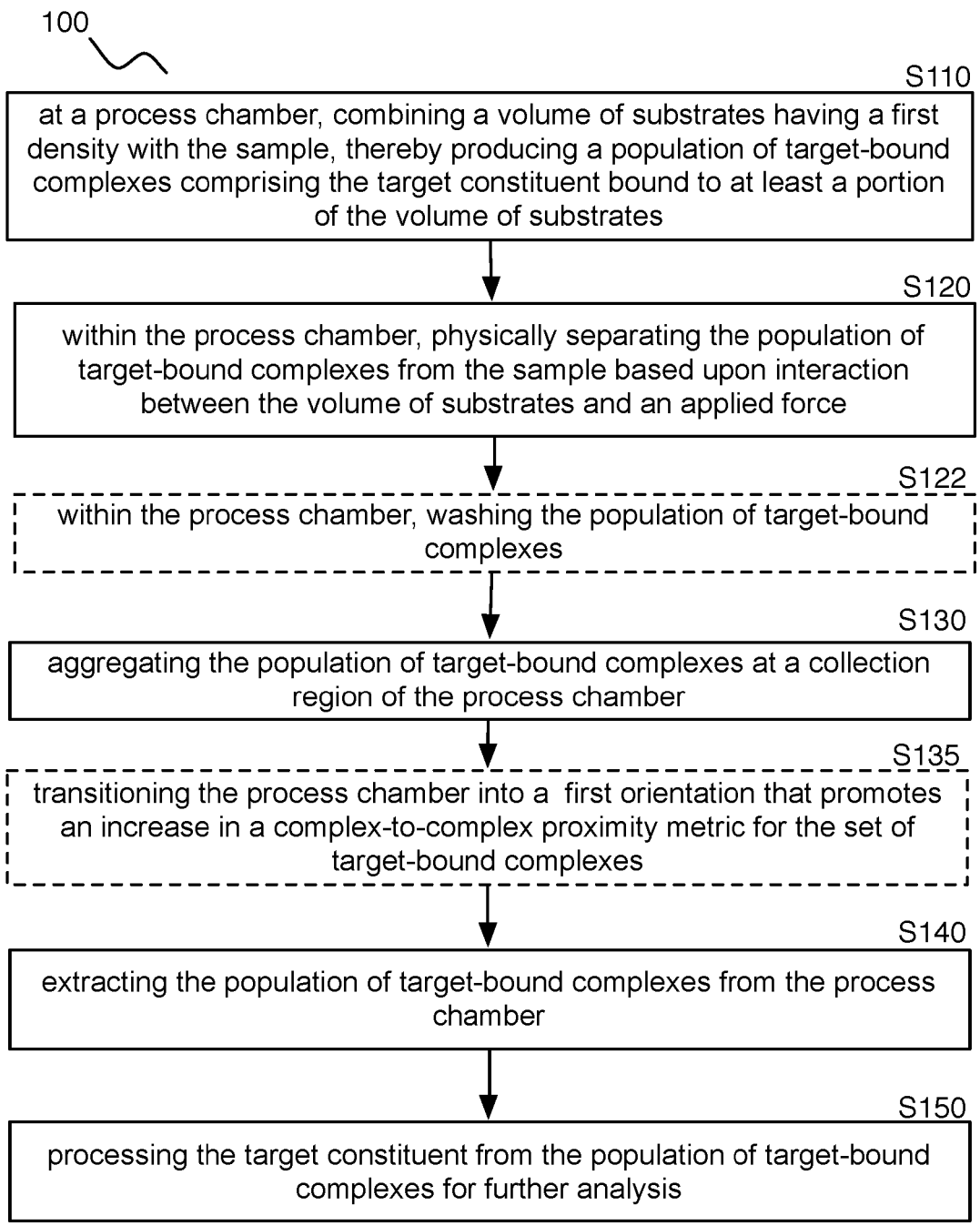

As shown in FIGS. 1A and 1B, an embodiment of a method 100 for buoyant separation of a target constituent of a sample comprises: at a process chamber, combining a volume of substrates having a first density with the sample, thereby producing a population of target-bound complexes comprising the target constituent bound to at least a portion of the volume of substrates S110; within the process chamber, physically separating the population of target-bound complexes from the sample based upon interaction between the volume of substrates and an applied force S120; aggregating the population of target-bound complexes at a collection region of the process chamber S130; extracting the population of target-bound complexes from the process chamber S140; and processing the target constituent from the population of target-bound complexes for further analysis S150.

The method 100 functions to provide a process for efficiently separating target constituents from a sample with a low amount of effort from research or clinical personnel. The method 100 also functions to facilitate downstream analyses (e.g., polymerase chain reaction-based assays, lateral flow assays, culture-based assays, etc.) of isolated and collected target constituents, for research applications, clinical applications, and/or food industry applications. Preferably, the method 100 can be applied to a large sample volume (e.g., 35 mL sample volumes, sample volumes over 5 mL, etc.), in order to extract one or more target components from the large sample volume. However, the method 100 can additionally or alternatively be applied to any other suitable sized sample volume (e.g., sample volumes smaller than or equal to 5 mL). The method 100 preferably utilizes passively applied forces (e.g., gravitational force) and/or actively applied forces (e.g., centrifugal force) to separate target constituents from a bulk sample based upon density differences between bound target constituents and the bulk sample; however, the method 100 can additionally or alternatively use any other physical parameter and associated separation mechanism to enhance isolation of a target constituent from a biological sample. For instance, in one variation, buoyant separation can be enhanced with magnetic manipulation of buoyant particles, by coupling a target constituent to particles having buoyant and magnetic-dual functionality. Upon separation of the target constituent from the sample, extraction of the target constituent can be performed according to the method 100. Additionally or alternatively, a non-target constituent of the sample can be tagged with magnetic substrates and drawn or repelled to a desired region of a process chamber (e.g., wall of the process chamber), while the target constituent that has been tagged with buoyant substrates is separated from the sample volume. However, any other suitable mode of separation process can be implemented in addition to or in substitution of the separation methods described.

Furthermore, the method 100 can be used to simultaneously or sequentially separate each of a set of target constituents from a bulk sample, based upon selective coupling of each of the set of target constituents to an associated substrate volume that can be individually isolated based upon a feature (e.g., physical feature, chemical feature, etc.). In variations, the method 100 can be used for separation of target cell and/or target analyte constituents from a biological sample, by using buoyant particles that facilitate concentration of the target constituents to a collection location (e.g., an extremum most opposite a gravitational or centrifugal force). The method 100 is preferably implemented, at least in part, using elements of the system 200 described in Section 2 below; however, the method 100 can additionally or alternatively be implemented using any other suitable system.

In a specific example, the method 100 can be used to provide buoyancy-activated separation and/or extraction of target components of a sample from a bulk sample volume of 1 Liter within 30 minutes. In a second specific example, the method 100 can be used to provide buoyancy-activated separation and/or extraction of target components of a sample from a bulk sample volume of 50 mL within 15 minutes. However, variations of the method 100 can alternatively be tuned to enable separation according to any other suitable timeline.

1.1 Method—Tagging with Buoyant Substrates

Block S110 recites: at a process chamber, combining a volume of substrates having a first density with the sample, thereby producing a population of target-bound complexes comprising the target constituent bound to at least a portion of the volume of substrates. Block S110 functions to provide interaction between the target constituent and the volume of substrates, thereby enabling selective manipulation of the target constituent in subsequent blocks of the method 100. Block S110 is preferably implemented using an embodiment, variation, and/or example of the process chamber described in Section 2 below; however, Block S110 can additionally or alternatively be implemented using any other suitable process chamber(s) for combination of a sample with a volume of a process material. Furthermore, variations of Block S110 can include receiving a sample volume having a population of target-bound complexes, where combination and/or complexification was performed in a separate process chamber.

In Block S110, combination preferably includes mixing of the target constituent with the volume of substrates in solution within the process chamber in order to provide sufficient interaction between the target constituent and the volume of substrates for coupling. In a specific example, particle binding to the volume of substrates of Block S110 is optimized when the ratio of substrates to targets is greater than 0.3; however, any other suitable substrate-target ratio may be used in variations of the specific example. In variations, mixing can include one or more of: rotary mixing about one or more axes of the process chamber; vortex mixing; mixing by agitation of the process chamber; mixing by rocking of the process chamber; mixing within a baffled vessel; mixing using aspiration and redelivery of a solution comprising the target constituent and volume of substrates (e.g., by way of a pipette); impellor mixing (e.g., with a blade configured in the process chamber, with a stir bar configured in the process chamber); acoustic mixing; any combination of the above described mixing types, and any other suitable mixing mechanism.

Preferably, combining the volume of substrates with the sample in Block S110 is performed in a manner that provides sufficient combination and dwell time to achieve sufficient complexification (i.e., forming of complexes) of the target constituent to the volume of substrates (e.g., with a desired binding efficiency). Furthermore, combination in Block S110 is preferably performed in a manner that prevents damage to (e.g., due to shear forces, due to other forces) or destruction of substrates of the volume of substrates and/or elements of the target constituent. Additionally, combining in Block S110 can be performed in a manner that prevents foaming of sample volumes, which can impede separation of the target constituent from the sample in subsequent blocks of the method according to buoyancy-based approaches. For instance, combining in Block S110 can be performed with a characteristic velocity (e.g., linear velocity, angular velocity) and/or below a desired level of acceleration of the process chamber in order to prevent foaming of the sample. However, combining in Block S110 can additionally or alternatively be performed in a manner that facilitates lysing of sample components (e.g., non-target sample components, target sample components where lysing releases the target constituent for binding to the volume of substrates). For instance, mixing to lyse untargeted sample components can facilitate subsequent separation of the untargeted sample components from the target constituents of the sample. Additionally or alternatively, lysing portions of the sample can facilitate release of the target constituent into solution for binding to the volume of substrates. However, combining in Block S110 can alternatively be performed in any other suitable manner.

In Block S110, substrates of the volume of substrates preferably comprise particle substrates (e.g., beads, spheres) characterized by a first density lower than that of the density (i.e., a second density) of fluid of the sample. As such, substrates of the volume of substrates are preferably configured to float within the sample to facilitate separation in subsequent blocks of the method 100. However, substrates of the volume of substrates can alternatively be configured with any other suitable density relative to that of the density of fluid and/or untargeted constituents of the sample to facilitate separation. In one variation, the volume of substrates comprises silica beads having a density less than that of fluid of the sample, wherein the silica beads are treated with a moiety (e.g., Streptavidin for biotin binding, an antibody for formation of an antibody-antigen complex, another moiety, etc.) configured to selectively couple with associated portions of the target constituent (e.g., cell, analyte) of the sample. In other variations, the volume of substrates can additionally or alternatively comprise substrates including any one or more of: plastic beads (e.g., polypropylene beads, polyethylene beads, etc.), glass beads, lipid beads (e.g., stabilized lipsome-based beads), hollow beads, solid beads, and any other suitable type of particle. Furthermore, moieties for binding to the target constituent can additionally or alternatively include any one or more of: charge-based moieties, nucleic acid-targeting moieties, protein-based moieties (e.g., cell adhesion molecules, growth factors), and any other suitable moiety. In examples, the particles of the volume of substrates have a diameter from 10 nm to 100 nm in targeting analytes or 1 μm to 30 μm in targeting cells; however, the particles can have any other suitable dimension configured facilitate efficient binding with elements of the target constituent. Furthermore, while substrates used in Block S110 are preferably particle substrates, Block S110 can additionally or alternatively include using planar or non-planar substrates (e.g., plates, surfaces), or substrates having any other suitable morphology that facilitates separation of the target constituent from the sample.

Behavior of substrates of the volume of substrates used in Block S110 can be governed according to expression [1], wherein $F_{buoyant}$ is the buoyant force in solution, p is the density of the substrate, g is the gravitational constant, and V is the volume occupied by the substrate:

$$F_{buoyant} = (\rho - 1)gV \quad [1]$$

Furthermore, a drag force on the substrate within the solution can be expressed according to expression [2], wherein $F_{drag}$ is the drag force, r is the radius of the substrate, and v is the velocity of the substrate in solution:

$$F_{drag} = 3\pi r \upsilon \quad [2]$$

However, substrates of the volume of substrates can alternatively be governed by any other suitable force expression related to buoyant forces or any other suitable force applied by the environment of the substrate.

In variations for multiplex separation and/or processing of a set of target constituents of the sample, the volume of substrates used in Block S110 can additionally or alternatively be configured to selectively bind to one of a set of target constituents of the sample. In one variation, the volume of substrates can comprise a first subset of substrates having a first density and processed with a first moiety configured to target a first target constituent, a second subset of substrates having a second density and processed with a second moiety configured to target a second target constituent, and any other suitable number of subsets of substrates having distinguishable densities and processed with specific moieties for targeting any other suitable number of target constituents of the sample. In one such example, the volume of substrates can include a first subset of substrates having a first density and processed with a moiety for targeting CD133+ expressing cells, a second subset of substrates having a second density (different form the first density) and processed with a moiety for targeting CD15+ expressing cells, and a third subset of substrates having a third density (different from the first and the second densities) and processed with moieties for targeting CD133+ and CD15+ expressing cells. In the example, specific subsets of the set of substrates can thus facilitate selective separation of cells expressing different biomarkers for further analysis. However, alternative variations of the volume of substrates can include subsets of substrates having any other features (e.g., physical feature, chemical feature, etc.) and configured to bind to different target constituents of the sample, in order to facilitate selective separation of different target constituents from the sample. Furthermore, in some variations, at least a subset of the volume of substrates can be configured to bind to and facilitate separation of an untargeted (e.g., waste, debris, etc.) portion of the sample.

As indicated above, Block S110 can be supported with and/or supplemented with alternative separation modes for extracting of a target constituent from the sample. For instance, in one variation, buoyant separation can be enhanced with magnetic manipulation of buoyant particles, by coupling the target constituent of the sample to buoyant particles and magnetically-responsive particles in Block S110. Separation in subsequent blocks of the method 100 can then be achieved with magnetic manipulation of the target constituent (e.g., attracting or repelling the target constituent to a region of the process chamber), removal of non-target components of the sample, and then extraction of the target constituent from the sample (e.g., due to buoyant separation of the target constituent from the sample upon removal of an applied magnetic field). Additionally or alternatively, in another variation, a non-target constituent of the sample can be tagged with magnetic substrates in Block S110 and drawn or repelled to a desired region of a process chamber (e.g., wall of the process chamber), while the target constituent that has been tagged with buoyant substrates is separated from the sample volume. However, any other suitable mode of complexification between target constituents and non-target constituents of the sample with binding moieties useful for separation can be implemented in addition to or in substitution of the methods described above.

In Block S110, combining can be supported by or supplemented with provision of environmental conditions and/or additional process reagents, to support subsequent processing steps and/or analysis of the target constituent. In one variation, mixing can be supplemented with modulating a temperature within the process chamber (e.g., to facilitate lysis or binding of the target constituent to the volume of substrates, to thermocycle the sample, etc.). Additionally or alternatively, mixing can include providing a lysing reagent (e.g., lysing solution, bead beating solution, etc.) within the process chamber, along with the sample and the volume of substrates, in order to facilitate lysis of undesired constituents of the sample and/or lysis of portions of the sample to release the target constituent for binding to the volume of substrates. Additionally or alternatively, mixing can include providing a fixing reagent (e.g., a cross-linking reagent) configured to fix portions of the sample. Additionally or alternatively, mixing can include providing a pH modulating reagent within the process chamber, and/or any other suitable reagent configured to provide a desired environment within the process chamber.

1.2 Method—Washing and Separation

Block S120 recites: within the process chamber, physically separating the population of target-bound complexes from the sample based upon interaction between the volume of substrates and an applied force. Similar to Block S110, Block S120 is preferably performed within an embodiment, variation, or example of the process chamber described in Section 2 below; however, Block S120 can additionally or alternatively be performed using any other suitable process chamber. Furthermore, while Blocks S110 and S120 are preferably implemented within the same process chamber, Blocks S110 and S120 can alternatively be implemented using separate process chambers. Block S120 functions to enable distinction of the population of target-bound complexes from other portions of the sample. In Block S120, physical separation can include promoting passive buoyant separation, within the process chamber, whereby the population of target-bound complexes experience buoyant forces due to effects of gravitational force on the volume of substrates having the first density, different from the densities of other untargeted constituents of the sample. Thus, a gravitational force can allow the population of target-bound complexes to move opposite a direction of the gravitational force for collection in Block S130.

Figure 6A:
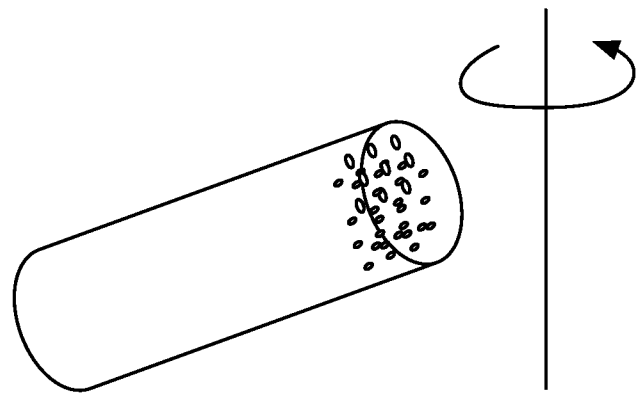
FIGS. 6A-6B depict variations of collection regions, dependent upon rotation axis, in an embodiment of a method for buoyant separation of a target constituent of a sample.
Figure 6B:
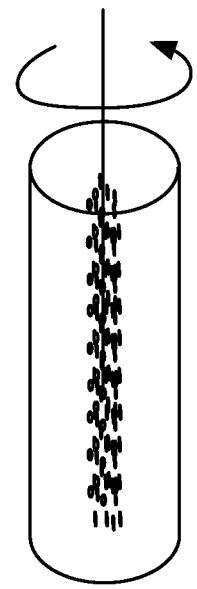

Additionally or alternatively, in Block S120, physical separation can include promoting active buoyant separation, within the process chamber, whereby the population of target-bound complexes experience buoyant forces due to effects of centrifugal force about an axis of rotation of the process chamber (e.g., as applied by a centrifuge interacting with the process chamber). Implementing active buoyant separation can further increase a separation effect over that of passive buoyant separation alone. In one such variation, as shown in FIG. 6B, Block S120 can include providing axial centrifugation about a longitudinal axis of the process chamber, wherein the axial centrifugation subjects the population of target-bound complexes to a buoyant force and allows the population of target-bound complexes to move opposite the direction of the applied centrifugal force (e.g., toward the longitudinal axis of the process chamber). In this variation, rectangular box geometries of the process chamber can facilitate maintenance of a substantially identical rate of rotation between fluid within the process chamber and the process chamber itself; however, any other suitable morphology of process chamber can be used, as described in more detail in Section 2 below. In another variation, Block S120 can include providing centrifugation about another axis (e.g., an axis displaced from the process chamber with any suitable orientation), wherein the centrifugation subjects the population of target-bound complexes to a buoyant force and allows the population of target-bound complexes to move opposite the direction of the applied centrifugal force (e.g., toward an extremum of the process chamber).

Additionally or alternatively, in Block S120, physical separation can include implementing a compound density gradient by introducing one or more fluids of varying density and/or miscibility into the process chamber. Introducing the one or more fluids promotes density-driven separation of components of the sample (i.e., the population of target-bound complexes, untargeted constituents, substrates, etc.) by creating a Ficoll-like gradient within the process chamber. In one example, introduction of a fluid having a density intermediate that of untargeted constituents and that of the population of target-bound complexes can enhance separation between the untargeted constituents and the complexes, wherein the fluid forms a barrier layer between the elements.

Additionally or alternatively, in Block S120, physical separation can include modulating a pressure within the process chamber, which can be used to promote mixing and/or enhance separation. In one operation, modulation of the pressure can shift the density of substrates of the volume of substrates to more closely match the density of fluid of the sample, thereby promoting more complete mixing. In another operation, modulation of the pressure can shift the density of substrates of the volume of substrate away from the density of fluid or untargeted constituents of the sample, thereby enhancing separation of the population of target-bound complexes. Separation in Block S120 can, however, be achieved using any other suitable additional or alternative mechanism.

In relation to separation in Block S120, embodiments of the method 100 can additionally or alternatively include Block S122, as shown in FIG. 1B, which recites: within the process chamber, washing the population of target-bound complexes. Block S122 functions to facilitate purification and/or enrichment of the population of target-bound complexes within the process chamber, prior to extraction of the population of target-bound complexes from the process chamber in subsequent blocks of the method 100. As such, Block S1222 can facilitate removal of the non-target constituents of the sample in promoting a higher degree of efficiency in extraction of the target constituent from the sample.

Figure 1C:
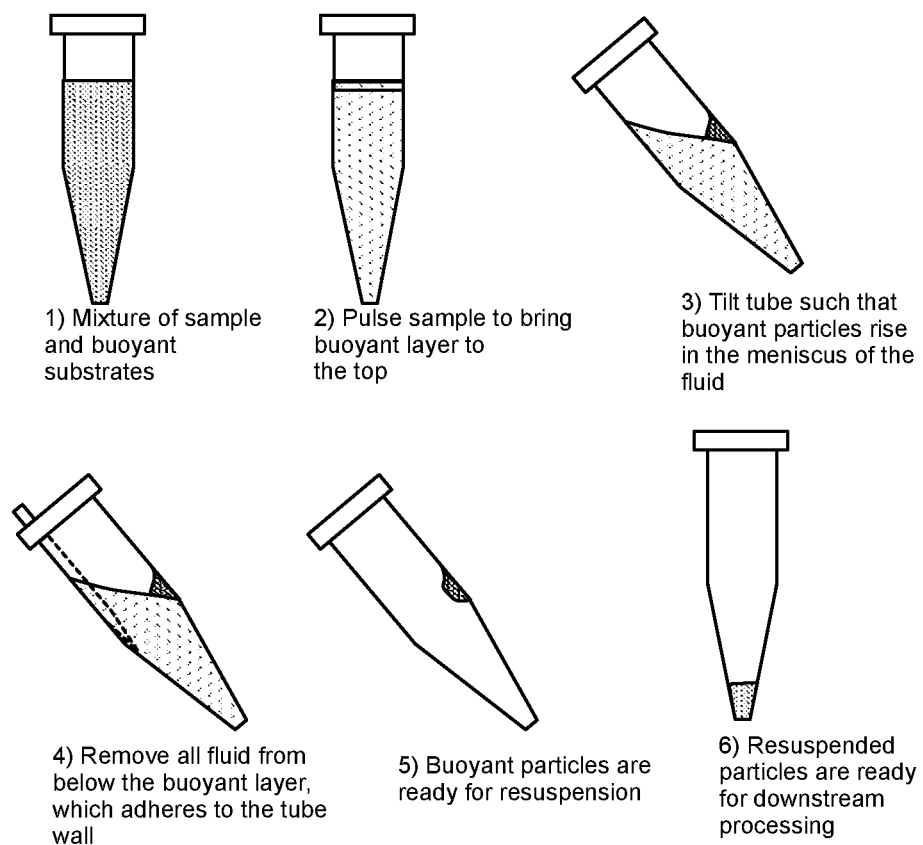
FIG. 1C depicts an example of a block of an embodiment of a method for buoyant separation of a target constituent of a sample.

Preferably, as shown in FIGS. 1B and 1C, Block S122 includes bringing the population of target-bound complexes to a desired region of the process chamber with an applied force; adjusting an orientation of the process chamber, thereby promoting the population of target-bound complexes to adhere to a wall of the process chamber; removing non-target portions of the sample from the process chamber; and resuspending the population of target-bound complexes within the process chamber with a suspension volume of fluid having a sufficiently high density. Washing in Block S122 can be performed any suitable number of times prior to extraction of the population of target-bound complexes in subsequent blocks of the method 100.

In Block S122, bringing the population of target-bound complexes to a desired region of the process chamber with an applied force can include allowing the population of target-bound complexes to undergo passive buoyant separation, within the process chamber, whereby the population of target-bound complexes experience buoyant forces due to effects of gravitational force on the volume of substrates having the first density, different from the densities of other untargeted constituents of the sample. Thus, a gravitational force can allow the population of target-bound complexes to move opposite a direction of the gravitational force in support of the washing operation of Block S122. Additionally or alternatively, in Block S122, physical separation can include promoting active buoyant separation, within the process chamber, whereby the population of target-bound complexes experience buoyant forces due to effects of centrifugal force about an axis of rotation of the process chamber (e.g., as applied by a centrifuge interacting with the process chamber). Additionally or alternatively, physical separation can be implemented in any other suitable manner.

In one such example, as shown in FIG. 1C, physical separation of the population of target-bound complexes can be enhanced with pulsing of the sample (e.g., with pulsing of the process chamber), to facilitate separation of the population of target-bound complexes at a region of the process chamber (e.g., an extremum of a liquid interface away from an applied gravitational force). In this example, the sample can be pulsed mechanically and/or acoustically. Furthermore, in the example, pulsing is performed for a short duration of time (e.g., below 5 seconds); however, variations of the example can include pulsing of the sample for any other suitable duration of time.

In Block S122, adjusting an orientation of the process chamber, functions to allow the population of target-bound complexes to adhere to a wall of the process chamber. In more detail, tilting of the process chamber can allow the population of target-bound complexes to aggregate at an anti-dependent rim of a fluid meniscus formed within the process chamber (e.g., an upper rim of a fluid meniscus in the orientation shown in FIG. 1C), after which removal of non-target portions of the sample from the process chamber can be performed (e.g., by pipetting, etc.). Thus, with gentle aspiration, non-target components of the sample, as well as a bulk of the sample fluid, can be removed from the process chamber while a substantially purified volume of the population of target-bound complexes is retained at the wall of the process chamber. Finally, the population of target-bound complexes can be washed from the wall of the process chamber and resuspended within a volume of fluid, where the volume of fluid is similar to, greater than, or substantially smaller than the original volume of fluid in the sample.

Additionally or alternatively, to enhance retention of the population of target-bound complexes at the process chamber during the washing process of Block S122, interior surfaces of the process chamber, proximal the collection region(s), can be patterned (e.g., roughened, texturized by etching, textured by molding, etc.) to enhance retention of the population of target-bound complexes at desired regions of the process chamber, as described in Section 2 below. Additionally or alternatively, retention of the target-bound complexes at regions of the process chamber can be enhanced by utilizing a recessed region or other region of the process chamber defining a separated interior volume of the process chamber, configured to retain the population of target-bound complexes during washing. Additionally or alternatively, washing in Block S122 can be enhanced by including a high molecular weight polymer with a washing solution, thereby promoting the generation of colloidal forces to reversibly enhance aggregation of the population of target-bound complexes within the fluid meniscus of the process chamber.

Block S122 can be performed manually (e.g., by an technician or other entity), or can alternatively be performed in an automated manner (e.g., with an automated system for adjusting the orientation of the process chamber, and with a fluid handling system for aspirating the non-target components of the sample/washing the target components of the sample). Block S122 can, however, be performed in any other suitable manner.

1.3 Method—Aggregation at a Collection Region

Block S130 recites: aggregating the population of target-bound complexes at a collection region of the process chamber, which functions to aggregate the population of target-bound complexes to at least one desired region of the process chamber, in order to facilitate extraction of the target constituent from the sample in an efficient manner. Interactions (e.g., hydrophobic interactions, hydrophilic interactions, neutral interactions) between fluid of the sample and the process chamber, and/or the method of separation (e.g., passive buoyant separation, active buoyant separation, compound density gradient, etc.) can affect the location(s) of the collection region(s) of the process chamber at which the population of target-bound complexes reside.

Figure 2A:
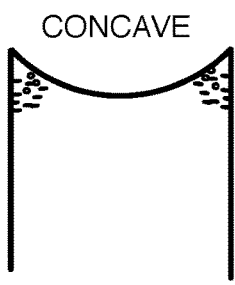
FIGS. 2A-2C depict variations of interactions between sample fluid and a process chamber in an embodiment of a method for buoyant separation of a target constituent of a sample.
Figure 2B:
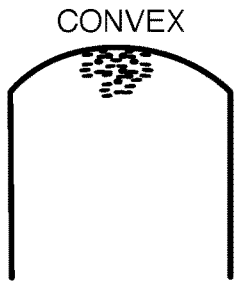
Figure 2C:
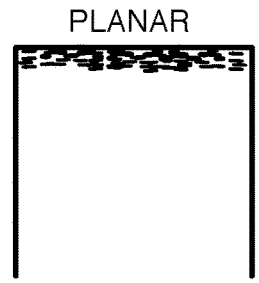

In some variations, implementation of passive buoyant separation in Block S120 can provide one or more collection region profiles, depending upon interaction of the process chamber with fluid of the sample. As shown in FIG. 2A, in variations of Block S120 that include a hydrophilic interaction between fluid of the sample and the process chamber, a concave meniscus formed at the fluid surface can provide a collection region at the perimeter of the fluid surface (e.g., a circular annular collection region for a cylindrical process chamber, a rectangular annular collection region for a rectangular prismatic process chamber, etc.) where clearing or an otherwise lower density population of target-bound complexes within the center of the meniscus can be used to extract bulk sample fluid and leave the population of target-bound complexes within the process chamber. As shown in FIG. 2B, in variations of Block S120 that include a hydrophobic interaction between fluid of the sample and the process chamber, a convex meniscus formed at the fluid surface can provide a collection region at the most superior portion of the fluid surface (e.g., an extremum of the fluid surface), where peripheral "clear" regions of the meniscus can be used to extract bulk sample fluid and leave the population of target-bound complexes within the process chamber. Examples of process chambers contributing to a concave or a convex fluid meniscus associated with a sample volume can include one or more of: a microwell plate, a microfabricated array, any other suitable well plate, any other suitable fabricated array, and any other suitable process chamber. As shown in FIG. 2C, in variations of Block S120 that include a neutral (e.g., non-hydrophobic, non-hydrophilic) interaction between fluid of the sample and the process chamber, a substantially planar surface formed at the fluid surface can provide a collection region at the fluid surface.

In any of the above variations, morphology and/or concentration of the collection region(s) can be enhanced by providing process chamber morphologies that affect the morphology(ies) of the collection region(s). For instance, in the examples shown in FIGS. 3A-3D, a conical process chamber morphology (e.g., linear conical, curved conical, etc.) with the vertex oriented at a superior portion of the process chamber can concentrate the collection region to a smaller region in comparison to a process chamber having a substantially constant or widening cross-section (i.e., in an inferior to superior direction) along a longitudinal axis of the process chamber. In one example, as shown in FIGS. 4A-4B, a frustoconical process chamber having a vertex oriented at a superior portion of the process chamber can concentrate the collection region, and an opening at the vertex of the frustoconical process chamber can enhance separation and facilitate collection of the population of target-bound complexes at the opening. Furthermore, overfilling of the frustoconical process chamber with the sample can provide a convex fluid surface at the opening, in the example, that effectively concentrates the population of target-bound complexes to a single location for extraction in Block S140. However, any other suitable morphology of process chamber, another example of which is shown in FIG. 5, can be used to produce any shape of collection region and/or any number of collection regions within a process chamber. Furthermore, interior surface features of the process chamber can enhance collection in Block S130. For example, a process chamber that has one or more recessed regions (e.g., scoring lines) at given positions (e.g., heights) along its interior surface can facilitate collection of the population of target-bound complexes within the recessed region(s) for later extraction in Block S140. In this example, the recessed regions can facilitate repeated separation and washing of the population of target-bound complexes within the process chamber.

In a specific example, aggregating the population of target-bound complexes can comprise aggregating the population of target-bound complexes at a superior portion of a process chamber (e.g., at a liquid-air interface of a sample volume within the process chamber), based upon passive buoyant separation. However, variations of the example can comprise any other suitable region for aggregation.

In variations of Block S120 implementing an active buoyant separation process, an axis or point about which the process chamber rotates governs the location of the collection region in Block S130. In particular, the population of target-bound complexes and/or substrates of the volume of substrates will migrate in a direction opposite that of a centrifugal or gravitational force. In one variation, wherein the process chamber rotates about a radial axis, as shown in FIG. 6A, lower density particles (e.g., particles of the population of target-bound complexes, substrates of the volume of substrates) in the sample move toward the radial axis and higher density particles move away from the radial axis. As such, the collection region in this variation is positioned at the portion(s) of the process chamber that were closest to the radial axis during rotation of the process chamber about the radial axis. In another variation, wherein the process chamber rotates about a longitudinal axis of the process chamber, as shown in FIG. 6B, lower density particles (e.g., particles of the population of target-bound complexes, substrates of the volume of substrates) in the sample move toward the longitudinal axis and higher density particles move away from the longitudinal axis. As such, the collection region in this variation is positioned at the portion(s) of the process chamber that were closest to the longitudinal axis during rotation of the process chamber about the longitudinal axis. Furthermore, in variations wherein rotation occurs about a longitudinal axis of the process chamber, a rate at which lower density particles float can be increased due to enhancement of buoyant effects resulting from increased proximity between multiple low density particles.

Figure 1D:
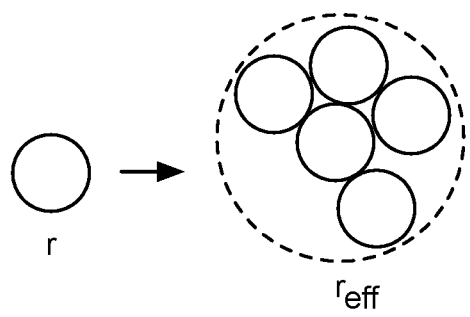
FIGS. 1D-1G depict an example of a block of an embodiment of a method for buoyant separation of a target constituent of a sample.
Figure 1E:
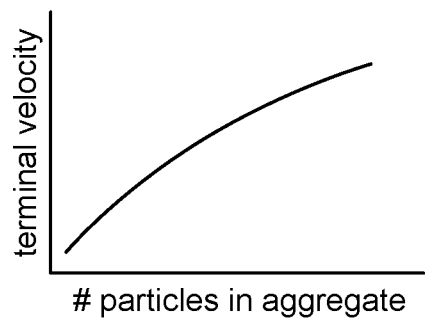

In more detail, and in relation to either passive or active buoyant separation, Block S130 can include enhancing a speed at which aggregation occurs by promoting a reduction in proximity between complexes of the population of target-bound complexes. As such, the method 100 can include Block S135, as shown in FIG. 1B, which recites: transitioning the process chamber into a first orientation that promotes an increase in a complex-to-complex proximity metric for the set of target-bound complexes. Block S135 can function to increase an effective radius, $r_{eff}$, and therefore, to increase an effective volume, $V_{eff}$, in relation to expression [i] above, thereby increasing the effective buoyant forces on aggregates of the population of target-bound complexes. As shown in FIGS. 1D-1E, as the number of buoyant particles within an aggregate increases, the net buoyant force, and therefore the terminal velocity of the aggregate increases, thereby enhancing a speed at which aggregation occurs.

Figure 1F:
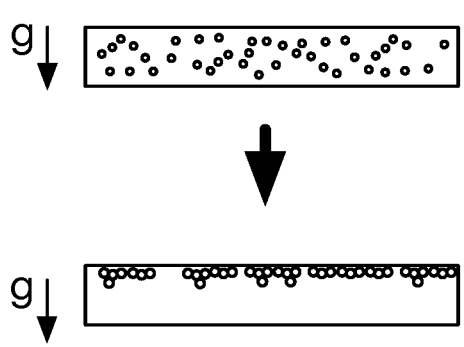
Figure 1G:
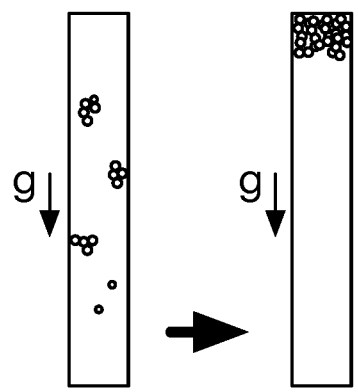

In one variation, as shown in FIGS. 1F-1G, Block S135 can include implementing a process chamber that has a high aspect ratio, wherein the process chamber is transitioned into a first orientation that promotes an increase in a complex-to-complex proximity metric for the set of target-bound complexes (e.g., the process chamber is transitioned onto its side). In this variation, the first orientation can be associated with an orientation wherein a short axis of the process chamber is substantially aligned with a direction of gravity (FIG. 1F). Maintenance of this orientation for a duration of time thus allows buoyant particles to move through the shortest possible distance in forming aggregates. Then, Block S135 can include transitioning the process chamber from the first orientation to a second orientation that drives the set of target-bound complexes toward a collection region of the process chamber (FIG. 1G). The second orientation can be associated with an orientation wherein a long axis of the process chamber is substantially aligned with a direction of gravity. This orientation thus allows the formed aggregates to aggregate toward the collection region of the process chamber in a manner that is more rapid than that of individual buoyant particles, due to a combination of hydrodynamic drafting among buoyant particles and the formation of transient particle aggregates with a much greater effective volume.

In other variations, Block S135 can additionally or alternatively include actively forming aggregates of subsets of the population of target-bound complexes based upon one or more of: centrifugation of the process chamber about any suitable axis; binding of multiple buoyant substrate particles to each unit of the target constituent of the sample; use of high-molecular weight polymer solutions that promote aggregation of the population of target-bound complexes in a reversible manner; and any other suitable means to promote aggregation. In relation to binding of multiple buoyant substrate particles to each unit of the target constituent of the sample, binding can be tunes such that rising of an aggregate within the process chamber only occurs when a desired number of buoyant components (e.g., 2 or more buoyant substrates) are coupled to a target. However, variations of Block S135 can additionally or alternatively be implemented in any other suitable manner. Furthermore, in any of the above variations of separation, separation can be used to indicate presence of the target constituent (e.g., using natural coloring of the target constituent, using stains, etc.), whereby monitoring of completion of a binding process based on completeness of a band of separation can additionally or alternatively be implemented.

1.4 Method—Extraction

Block S140 recites: extracting the population of target-bound complexes from the process chamber, which functions to remove the population of target-bound complexes from other portions of the sample, or to remove portions of the sample from the population of target-bound complexes, thereby generating an enriched volume comprising the population of target-bound complexes. Block S140 preferably includes transmitting a target constituent extractor into the process chamber, concentrating the population of target-bound complexes at a region of the target constituent extractor, and delivering the population of target-bound complexes from the target constituent extractor for downstream processing.

In one variation, as described in more detail in Section 2 below, the target constituent extractor includes opposing frustoconical surfaces configured to facilitate concentration and extraction of the population of target-bound complexes from the process chamber. In one example of this variation, the target constituent extractor can include a threaded region 600 that complements threads of the process chamber (e.g., a 50 mL tube), such that transmitting the target constituent extractor includes rotating the target constituent extractor relative to the process chamber in order to engage their complementary threads. In another example of this variation, the target constituent extractor may omit threads, transmitting the target constituent extractor into the process chamber can include translating the target constituent extractor concentrically into an opening of the process chamber. Transmitting the target constituent extractor into the process chamber can, however, be implemented in any other suitable manner.

In relation to the variation described above, concentrating the population of target-bound complexes at a region of the target constituent extractor can include concentrating the set of target-bound complexes at a region of a frustoconical surface of the target constituent extractor, wherein the target constituent extractor has an inverted frustoconical surface opposing and coupled to the frustoconical surface by a channel. Then, to facilitate delivery of the population of target-bound complexes from the target constituent extractor, a fluid level within the inverted frustoconical surface can be adjusted, in order to bring the population of target-bound complexes into the inverted frustoconical surface for extraction. In one example, the fluid level can be adjusted upon receiving an additional fluid volume into the channel of the target constituent extractor connecting the two frustoconical surfaces, thereby delivering the population of target-bound complexes from the frustoconical surface and into the inverted frustoconical surface by way of the channel. In another example, the fluid level can be adjusted by translating the target constituent extractor deeper into the process chamber, thereby delivering the population of target-bound complexes from the frustoconical surface and into the inverted frustoconical surface by way of the channel. In another example, wherein the process chamber is deformable (e.g., squeezable), the fluid level can be adjusted upon deformation of the process chamber (e.g., squeezing of the process chamber), thereby delivering the population of target-bound complexes from the frustoconical surface and into the inverted frustoconical surface by way of the channel. However, adjusting the fluid level can additionally or alternatively be implemented in any other suitable manner.

Finally, in Block S140, delivering the population of target-bound complexes from the target constituent extractor for downstream processing can include delivering the population of target-bound complexes into a pipette for extraction of the population of target-bound complexes from the target-constituent extractor. Additionally or alternatively, in a variations of the target constituent extractor including a separate extraction component having a second inverted frustoconical surface 376' opposing the inverted frustoconical surface 366', and delivering the population of target-bound complexes can include delivering the population of target-bound complexes into the second inverted frustoconical surface of the separate extraction component (e.g., without involvement of a pipette). Variations of extraction of the population of target-bound complexes can, however, be implemented in any other suitable manner.

1.4.1 Extraction—Additional Examples

In removing fluid (e.g., fluid containing the population of target-bound complexes, fluid excluding the population of target-bound complexes) using the target constituent extractor, removal can include active fluid removal (e.g., by pipetting, by capillary action, etc.). Additionally or alternatively, fluid removal can include surface contact methods, whereby an extraction element (e.g., target constituent extractor described below) makes surface contact with fluid of the sample in order to provide extraction. In extraction, fluidic transfer can occur through 1) wetting/capillary forces when an extraction element (e.g., extraction vessel, extraction membrane) makes contact with the collection region containing the population of target-bound complexes and/or 2) further climbing of buoyant elements (e.g., the population of target-bound complexes, substrates of the volume of substrates) within an extraction element. Extraction elements can include one or more of: solid substrates with or without a patterned surface (e.g., a glass substrate with a Teflon pattern to define an active extraction region); capillary structures (e.g., an element with a tubular geometry); annular elements (e.g., a ring, a circular annular element, a rectangular annular element, etc.); and any other suitable element configured to promote fluid transfer.

Figure 7A:
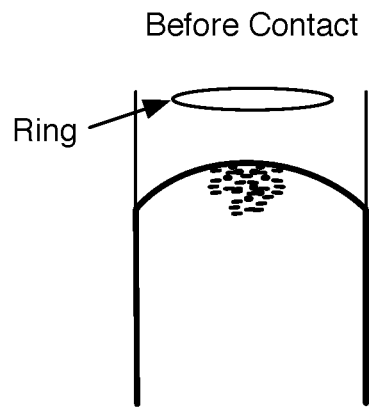
FIGS. 7A-7B depict a variation of extraction in an embodiment of a method for buoyant separation of a target constituent of a sample.
Figure 7B:
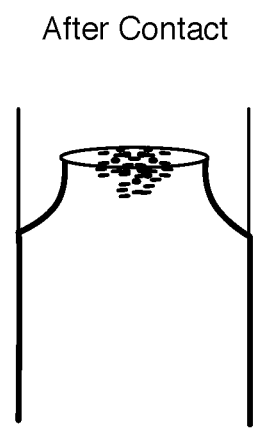

As such, in one example of Block S140 using an annular extraction element (e.g., a ring), extracting the population of target-bound complexes can include bringing the annular extraction element into contact with a fluid surface of the sample, proximal the collection region, as shown in FIG. 7A, which induces interaction between fluid surrounding the population of target-bound complexes and the annular extraction element. After contact has been made between the annular extraction element and the fluid surface, elevating the annular extraction element (e.g., in an inferior-to-superior direction) can allow the population of target-bound complexes to climb and further separate from other portions of the sample, due to surface tension enabled by the annular extraction element, as shown in FIG. 7B.

In another example of Block S140 using a wicking extraction element (e.g., a permeable substrate), extracting the population of target-bound complexes can include bringing a cellulosic or synthetic fiber wicking extraction element (e.g., a swab, fabric, etc.) into contact with a fluid surface of the sample, proximal the collection region. As such, the wicking extraction element can facilitate passive influx of fluid from the sample, with the population of target-bound complexes, during permeation of the wicking extraction element. In a related example, a "loading region" of a strip-based end point assay (e.g., a lateral flow immunoassay), can function as a wicking extraction element for simultaneous extraction of the population of target-bound complexes and preparation of the population of target-bound complexes for interrogation.

In another example of Block S140 using a sieve extraction element (e.g., a porated surface), extracting the population of target-bound complexes can include bringing a sieve into contact with a fluid surface of the sample, proximal the collection region. As such, the sieve can provide a plurality of openings at a surface of the sieve, wherein the openings draw fluid from the sample into the sieve and allow passive influx of the population of target-bound complexes into the sieve.

In another example of Block S140 using a membrane extraction element (e.g., a thin-film membrane), extracting the population of target-bound complexes can include bringing a membrane into contact with a fluid surface of the sample proximal the collection region, wherein the surface of the membrane has been chemically (e.g., with particle attracting moieties) and/or physically (e.g., texturally, in relation to porosity, etc.) prepared to enhance extraction. After a period of interaction between the membrane and the fluid surface, the membrane, with the population of target-bound complexes, can then be retrieved for further processing and/or a downstream application using the population of target-bound complexes.

In another example of Block S140, a freely floating membrane (e.g., a membrane similar in size to an opening of the process chamber proximal the collection region) can rest within the process chamber (e.g., at a fluid surface proximal the collection region) and passively collect the population of target-bound complexes as they migrate toward the collection region. In an alternative variation of this example, the membrane can be retained away from the collection region (e.g., retained at an inferior portion of the process chamber), and released toward the collection region after aggregation of the population of target-bound complexes at the collection region as progressed to a sufficient state. In either of these examples, when a sufficient proportion of the population of target-bound complexes have been gathered at the freely floating membrane, the membrane can be retrieved (e.g., using forceps, using tweezers) from the process chamber for further processing and/or analysis of the population of target-bound complexes.

Figure 8:
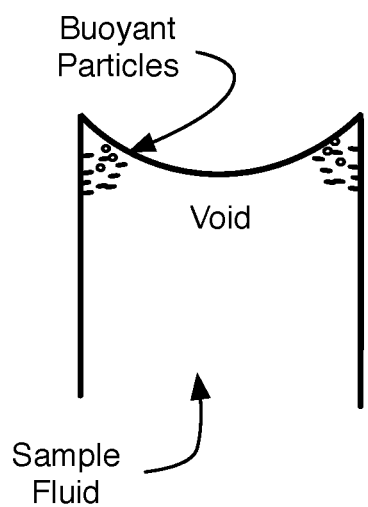
FIG. 8 depicts a variation of extraction in an embodiment of a method for buoyant separation of a target constituent of a sample.

In another example of Block S140 wherein a hydrophilic interaction occurs between fluid of the sample and the process chamber, a region substantially void of the population target-bound complexes can be created proximal a central longitudinal axis of the process chamber, as shown in FIG. 8. In this example, extraction can comprise removal of fluid from the region that is void of the population of target-bound complexes, thus concentrating the population of target-bound complexes within the process chamber. To enhance retention of the population of target-bound complexes at the process chamber, interior surfaces of the process chamber, proximal the collection region(s), can be patterned (e.g., roughened, texturized by etching, textured by molding, etc.) to enhance retention of the population of target-bound complexes at the process chamber. Furthermore, in this example, single-instance or repeated washing (e.g., with a wash buffer) and extraction of fluid from the region that is void of the population of target-bound complexes can further enrich the population of target-bound complexes within the process chamber, as described in relation to Block S122 above. Furthermore, automation of the fluid extraction process (e.g., with an automated liquid handling system) can further remove burden for a technician or other entity associated with the example of Block S140.

In another example of Block S140, extracting the population of target-bound complexes can implement a collection region chamber of the process chamber, whereby the collection region chamber receives the population of target-bound complexes in Block S130. In an example, the process chamber can comprise a cap (e.g., a cap positioned at a most superior portion of the process chamber) that receives the population of target-bound complexes in Block S130, by way of passive buoyant separation and/or centrifugation about a radial axis. After collection is complete and a sufficient proportion of the population of target-bound complexes have entered the cap, extraction can include dissociation of the cap from the process chamber to complete extraction.

In another example of Block S140, extracting the population of target-bound complexes can involve use of a pipette tip (or other fluid aspiration and delivery element) to facilitate extraction and/or separation. In the example, fluid of the sample from the process chamber, with the population of target-bound complexes, can be aspirated into the pipette tip, and retained therein to facilitate buoyant separation of the buoyant particles (i.e., coupled to the target constituent) from non target constituents of the sample fluid. After separation has progressed to a sufficient degree, sample fluid substantially void of the population of target-bound complexes can be expelled from the pipette tip, leaving the population of target-bound complexes within the pipette tip. Finally, the population of target-bound complexes can be processed (e.g., after delivery from the pipette tip) for a downstream application, as described in subsequent blocks of the method 100. In variations of this example, mixing, by drawing a wash reagent into the pipette tip and delivering the wash reagent from the pipette tip, can further facilitate purification and separation of the population of target-bound complexes from the sample.

While several extraction elements and methods of use are described, any other suitable combination of the above described extraction elements, and/or any other suitable extraction element(s) can facilitate extraction of the population of target-bound complexes in Block S140. Furthermore, while the above Blocks are described in distinction from each other, any one or more of the embodiments, variations, and/or examples of Blocks S110-S140 can be performed substantially simultaneously with each other, in order to provide an efficient sample processing mechanism. As such, in some variations, a process chamber used in the method 100 can be module and comprise a first portion for collection and a second portion for extraction of the population of target-bound complexes, such that collection and extraction can occur simultaneously within a single process chamber. In some variations, the process chamber can further be configured to facilitate simultaneous combination of the volume of substrates with the target constituent, and collection of the population of target-bound complexes, by simultaneously mixing and driving the population of target-bound complexes toward the collection region(s). Simultaneous performance of multiple blocks of the method 100 can, however, be implemented in any other suitable manner.

1.5 Method—Downstream Processing

Block S150 recites: processing the target constituent from the population of target-bound complexes for further analysis. Block S150 functions to provide a means for subsequent processing of the target constituent of the sample for a downstream application. Block S150 can comprise one or more of: Block S160, which recites resuspending the population of target-bound complexes for at least one of analysis and storage; and Block S170, which recites generating an analysis of the target constituent upon processing of the population of target-bound complexes. In Block S160, resuspending the population of target-bound complexes can include transferring the population of target-bound complexes to a buffer solution or transferring a buffer solution to the population of target-bound complexes. Additionally or alternatively, resuspending can include bringing an elution solution into contact with the population of target-bound complexes, in order to separate the target constituent(s) of the sample from substrates of the volume of substrates. Elution of the target constituent would thus enable analysis of the target constituent in isolation from substrates of the volume of substrates. Resuspending in Block S160 can further include washing the population of target-bound complexes and/or the target constituent, or include any other suitable steps that prepare the target constituent or complexes for storage or further analysis.

In Block S170, generating the analysis can include any one or more of: performing a light-based assay (e.g., fluorescence-based assay, photometric assay, etc.) of the target constituent; amplifying and/or sequencing nucleic acid content of the target constituent of the sample; performing a molecular diagnostic assay of nucleic acid content of the target constituent; performing a biochemical assay configured to identify compositional aspects of the target constituent; performing a cytometric assessment of particles of the population of target-bound complexes or the target constituent; culturing and/or expanding the target constituent; and performing any other suitable tissue-level, cellular-level, protein-level, and/or molecular-level assessment of the target constituent of the sample.

Figure 9A:
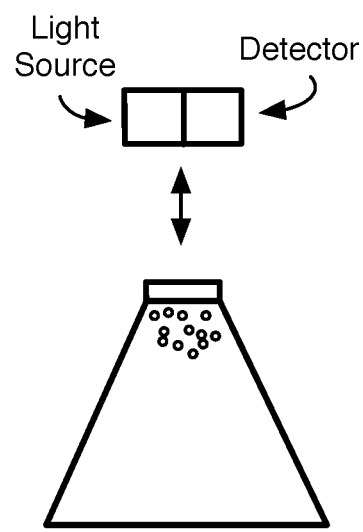
FIG. 9A-9B depict variations of a process chamber comprising a detection window in an embodiment of a method for buoyant separation of a target constituent of a sample.
Figure 9B:
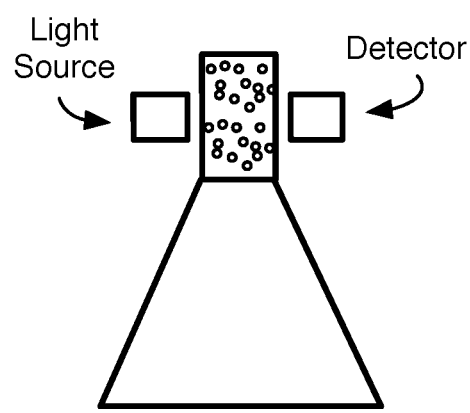

In one example of Block S170, the process chamber used in blocks of the method 100 can include a window at which the target constituent and/or portions of the population of target-bound complexes can be directed and/or detected for interrogation. The window thus allows imaging (e.g., fluorescent imaging, optical imaging, etc.) or other observation of the target constituent, in a manner that does not require extraction of the target constituent from the process chamber. In two example process chambers used in Block S170, a window at a superior portion of the process chambers, proximal the collection region of the process chamber, can allow observation and interrogation of the target constituent at the window. In a first example process chamber, the window is a substantially planar and optically transparent surface that abuts the collection region, as shown in FIG. 9A. In a second example process chamber, as shown in FIG. 9B, the window defines a volume superior to the collection region into which the target constituent, bound to the volume of substrates, can migrate for further observation and interrogation. Variations of the examples of Block S170 can, however, be performed in any other suitable manner, using any other suitable process chamber.

In some variations the method 100 can include carrying out surface chemistry and/or other modifications to substrates of the volume of substrates, in order to enhance processing and separation of the target constituent from the sample. Such modifications can be implemented using process chamber morphologies, described further in Section 2 below, which allow multistep modifications to be performed on substrate surfaces without requiring direct handling of the substrates. As such, handling of buoyant substrates can be performed in a manner that reduces product loss and handling of potentially harmful reagents. In one such variation, a process chamber having a dip tube that provides access to fluid within the process chamber, below an active collection region at which buoyant substrates aggregate, can enable fluid transfer in the process chamber substantially without disturbance of the buoyant substrates. In examples, the dip tube can be incorporated into a lid of the process chamber, as shown in FIG. 12A, incorporated into a wall of the process chamber, as shown in FIG. 12B, be a modular component that interfaces with the process chamber (e.g., by adhering to a wall of the process chamber with a membrane), and/or cooperate with the process chamber in any other suitable manner.

Figure 10:
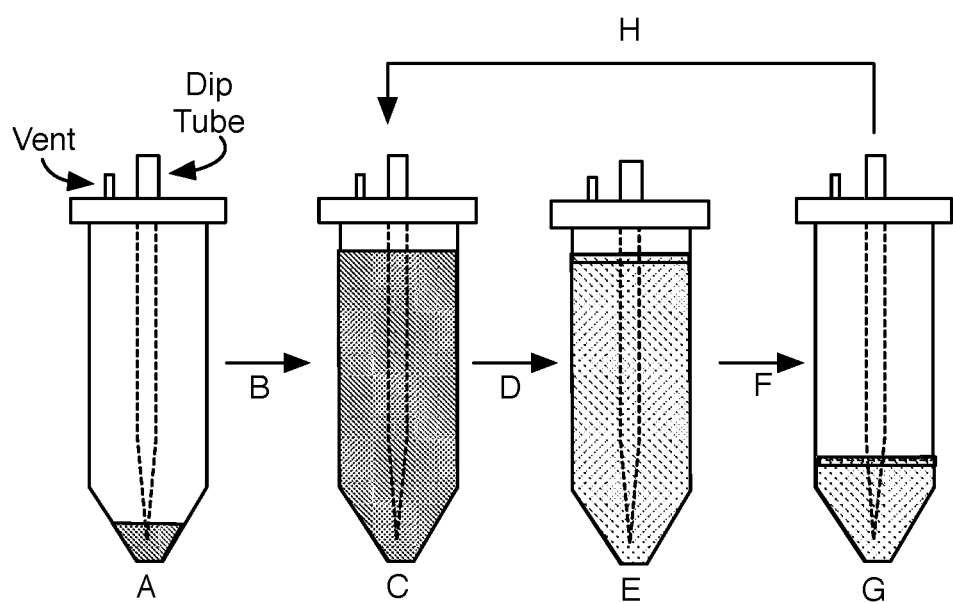
FIG. 10 depicts a variation of a method for substrate modification in a method for buoyant separation of a target constituent of a sample.

In one example workflow for modification of a buoyant substrate, as shown in FIG. 10, the method can include introducing buoyant substrates (e.g., beads in powder form, beads suspended in liquid) into the process chamber (A); adding a first reaction solvent and associated reactants into the process chamber, by way of a dip tube coupled to the process chamber (B); incubating the buoyant substrates with the first reaction solvent to achieve chemical modification (C); centrifuging the process chamber (D) to achieve separation of the modified buoyant substrates (E); removing excess portions of the first reaction solvent and reactants from the process chamber, by way of the dip tube (F); preparing the process chamber for additional modification solvents and reactions (G); and repeating steps (A)-(G) as necessary (H).

The method 100, can, however, include any other suitable Blocks or Steps for separating a target constituent from a sample based upon buoyancy and/or any other separation mechanism, and generating an analysis based upon processing of the target constituent. Furthermore, as a person skilled in the art will recognize from the previous detailed description and from the figures, modifications and changes can be made to the method 100 without departing from the scope of the method 100.

2. System

Figure 3A:
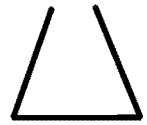
FIGS. 3A-3D depict variations of a process chamber morphological configurations in embodiments of a system and method for buoyant separation of a target constituent of a sample.
Figure 3B:
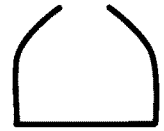
Figure 3D:
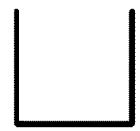
Figure 3C:
Figure 11:
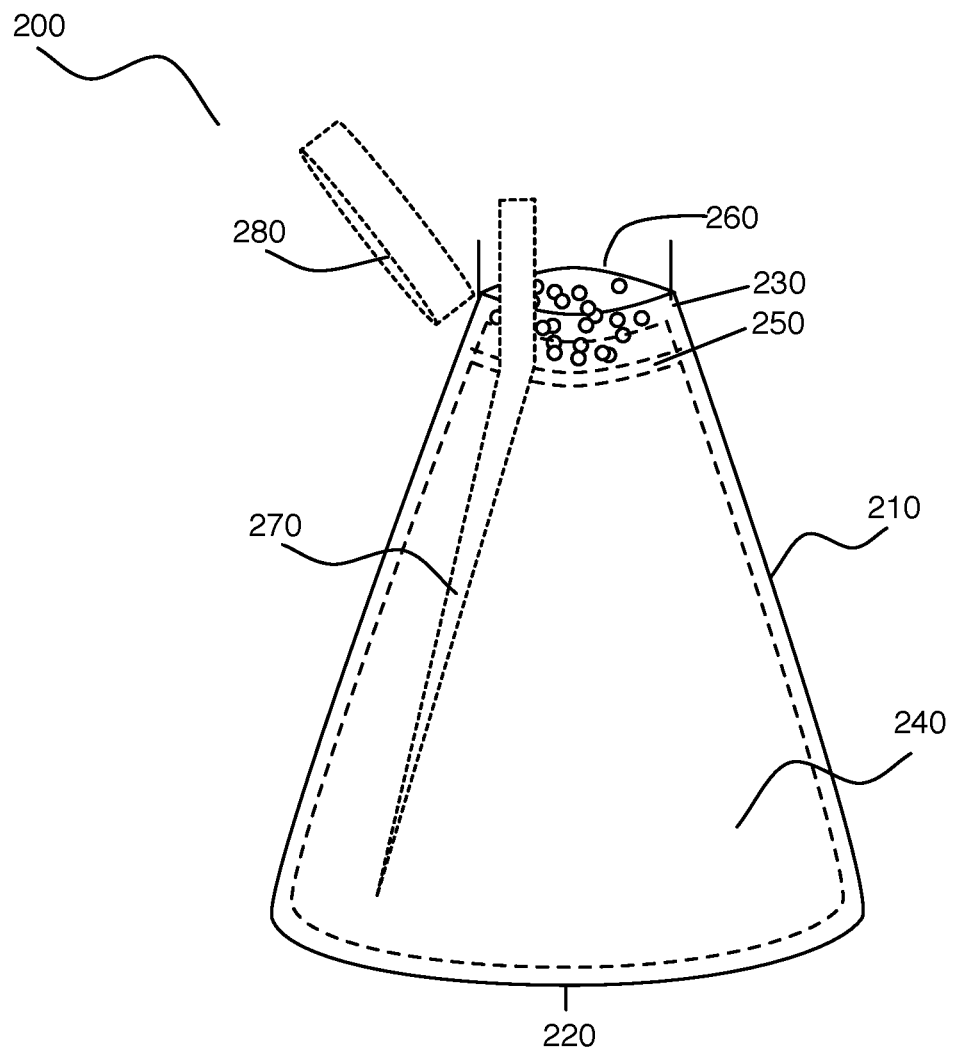
FIG. 11 depicts a first embodiment of a system for buoyant separation of a target constituent of a sample.
Figure 14:
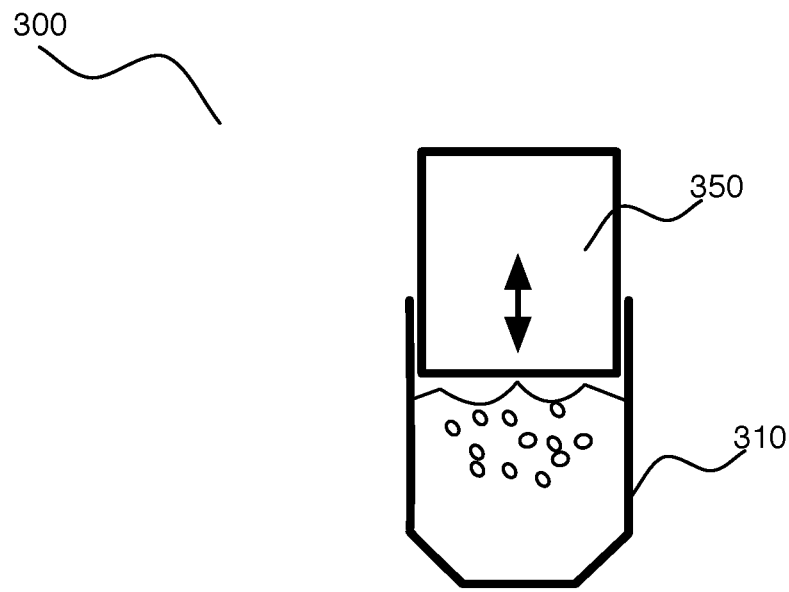
FIG. 14 depicts a second embodiment of a system for buoyant separation of a target constituent of a sample.

As shown in FIG. 11, an embodiment of a process chamber 200 for buoyant separation of a target constituent of a sample comprises: a frustoconical surface 210 defining a base region 220 having a first width and a collection region 230 having a second width, narrower than the first width, in opposition to the base region, wherein the frustoconical surface defines a volume 240 configured to receive the sample having the target constituent. In variations, the frustoconical surface can have a straight profile in elevation, as shown in FIGS. 3A and 3D. Alternatively, the frustoconical surface can have a curved profile or any other suitable profile in elevation, as shown in FIGS. 3B and 3C. The volume 240 defined within the process chamber 200 preferably has a low height-to-width ratio, in order to facilitate rapid separation of the target constituent from the sample (e.g., by providing a smaller traveling distance for a given volume). However, the volume 240 defined within the process chamber 200 can alternatively have a high height-to-width ratio (e.g., as a slender volume), or any other suitable height-to-width ratio.

In variations, an interior surface of the frustoconical surface 210 can include at least one recessed feature 250 (e.g., a slot, a textured surface) configured to enable retention of a population of target-bound complexes generated during combination of the target constituent of the sample with a volume of buoyant substrates within the process chamber. Additionally or alternatively, in some variations, the process chamber 200 can include a window 260 configured adjacent to the collection region 230, wherein the window comprises a planar substrate configured to enable observation of target-bound complexes aggregated at the collection region, as shown in FIG. 9A, or alternatively defines a detection volume configured to receive the population of target-bound complexes from the collection region and to interface with a detector module, as shown in FIG. 9B.

Additionally or alternatively, in some variations, the process chamber can comprise or be coupled to a dip tube 270 comprising a first end that couples to a fluid transfer element (e.g., a pipette tip) and a second end configured inferior to the collection region at which buoyant substrates aggregate, in order to enable fluid transfer in the process chamber substantially without disturbance of the buoyant substrates. In examples, the dip tube can be incorporated into a lid of the process chamber, as shown in FIG. 12A, incorporated into a wall of the process chamber, as shown in FIG. 12B, be a modular component that interfaces with the process chamber (e.g., by adhering to a wall of the process chamber with a membrane), and/or cooperate with the process chamber in any other suitable manner.

Additionally or alternatively, in some variations, the process chamber 200 can comprise a cap 280 in communication with the collection region, wherein the cap 280 facilitates extraction of the population of target-bound complexes from the collection region of the process chamber. An additional example of a portion of the process chamber is shown in FIG. 13.

In related embodiments of a system 300 for separating and extracting a population of target-bound complexes from a sample, embodiments and variations of which are shown in FIGS. 14-17C, the system 300 can include a process chamber 310 and an extraction apparatus 350 configured to interface with the sample containing chamber 310 in different operation modes, in order to facilitate separation and/or enable extraction of a population of target-bound complexes from the sample. Alternative variations of these embodiments of the system 300 can, however, omit the process chamber 310.

In the related embodiments of the system 300, the process chamber 310 functions to hold a sample and can additionally or alternatively function to facilitate mixing of the target constituent of the sample with a volume of buoyant substrates to produce a population of target-bound complexes. The process chamber 310 preferably has a closed end and an openable end (e.g., an end configured to be opened, a permanently open end, etc.) opposing the closed end, the process chamber configured to hold the sample having the target constituent and facilitate binding of the target constituent to a set of substrates to produce a set of buoyant target-bound complexes. The process chamber 310 is preferably substantially rigid; however, the process chamber can alternatively be deformable (e.g., under compression, under tension, under torsion, etc.). In a specific example, the process chamber 310 is composed of plastic; however, the process chamber 310 can alternatively include regions composed of one or more of: a ceramic material, a metallic material (e.g., to aid magnetic separation), and any other suitable material. Furthermore, the process chamber 310 can additionally or alternatively be configured in any other suitable manner.

In the related embodiments of the system 300, the extraction apparatus 350 (i.e., target constituent extractor) functions to provide a surface or volume at which or into which the population of target-bound complexes can be transmitted, thereby facilitating extraction of the population of target-bound complexes from a bulk volume of the sample. In the related embodiments, the extraction apparatus can comprise elements and/or be configured in any other suitable manner (e.g., with surface treatments) that enable retention of the population of target-bound complexes at the extraction apparatus 350.

In a first variation, as shown in FIGS. 15A-15D, the system 300' includes a sample containing chamber 310' defining a volume for retention of the sample, within which the target constituent(s) of the sample can be combined with a volume of buoyant substrates that enable isolation of the target constituent from the sample in the form of a population of target-bound complexes. In the first variation, the extraction apparatus 350' comprises a first portion 360' including a frustoconical surface 362' that defines a feeding region 363' into an opening 364' (e.g., having an inverted frustoconical surface that opposes the frustoconical surface 362') at a superior portion of the first portion 360'; and a second portion 370' comprising a collection tube 372' that interacts with the opening 364' of the feeding region 363' to receive particles of the population of target-bound complexes from the sample. In the first variation, the frustoconical surface defines a base region that interfaces with the sample volume in the process chamber 310', and a concentration region (associated with the opening 364') above and in opposition to the base region, wherein the frustoconical surface defines a volume configured to concentrate the set of buoyant target-bound complexes at the concentration region of the frustoconical surface. Furthermore, in the first variation, the extraction apparatus 350' can include a separation zone having an inverted frustoconical surface 366', in communication with the concentration region of the frustoconical surface 362' by a channel 365' that transmits the set of buoyant target-bound complexes into the separation zone, for removal of the set of buoyant target-bound complexes from the concentration region. In the first variation, the second portion 370' of the extraction apparatus 360' can include a venting chamber 374' configured to provide venting of the sample containing chamber 310' during relative displacement between the sample containing chamber and the extraction apparatus 350' for extraction of the population of target-bound complexes from the sample.

Figure 15A:
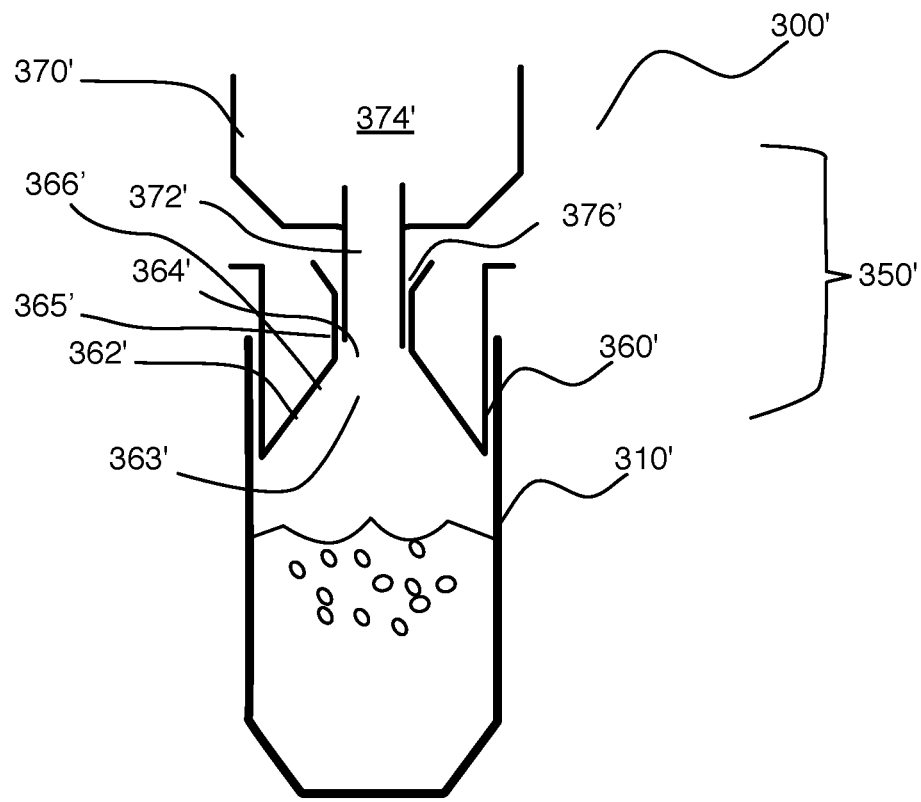
FIGS. 15A-15D depict a first variation of an embodiment of a system for buoyant separation of a target constituent of a sample.
Figure 15B:
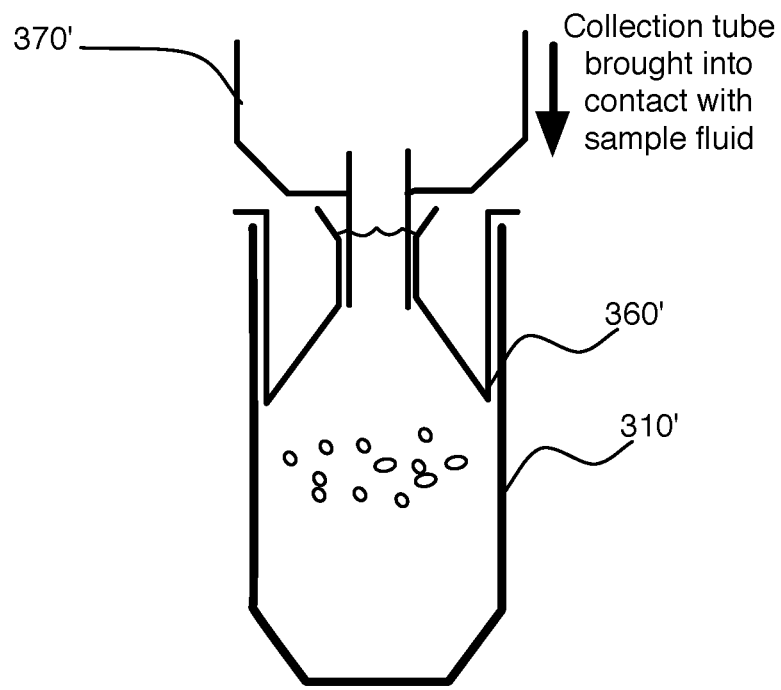
Figure 15C:
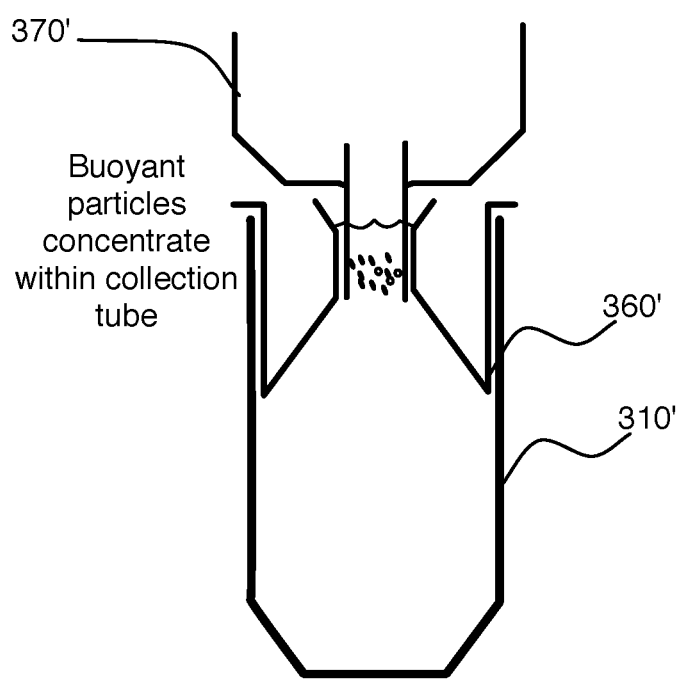
Figure 15D:
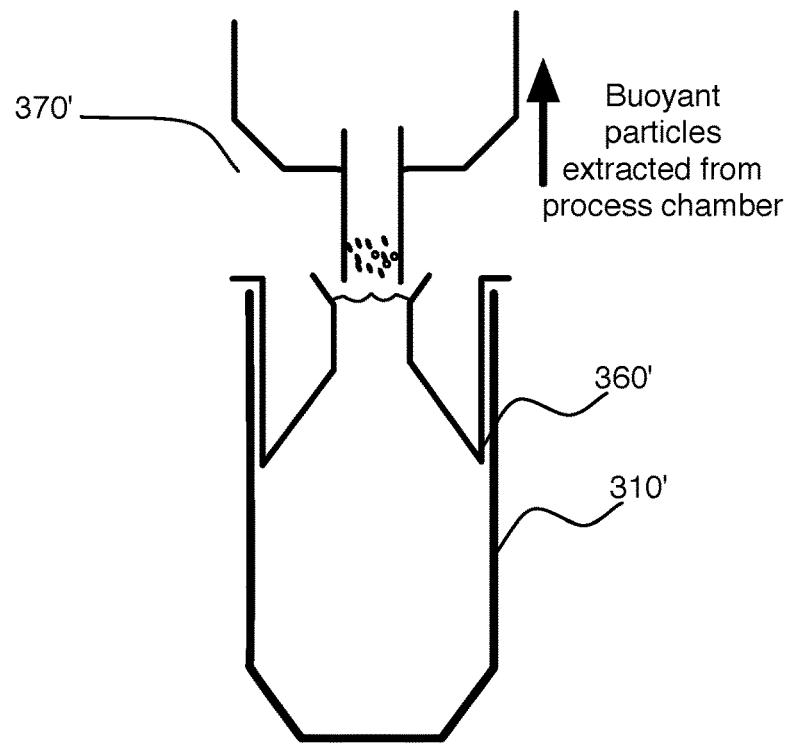
Figure 15E:
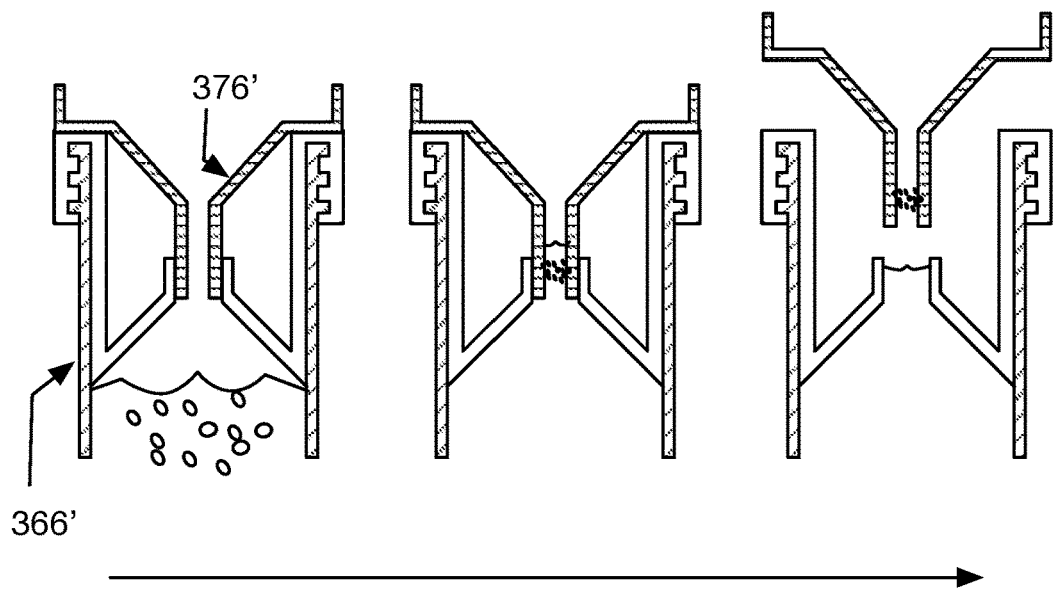
FIG. 15E depicts an example related to the first variation of an embodiment of a system for buoyant separation of a target constituent of a sample.
Figures 16A, 16B:
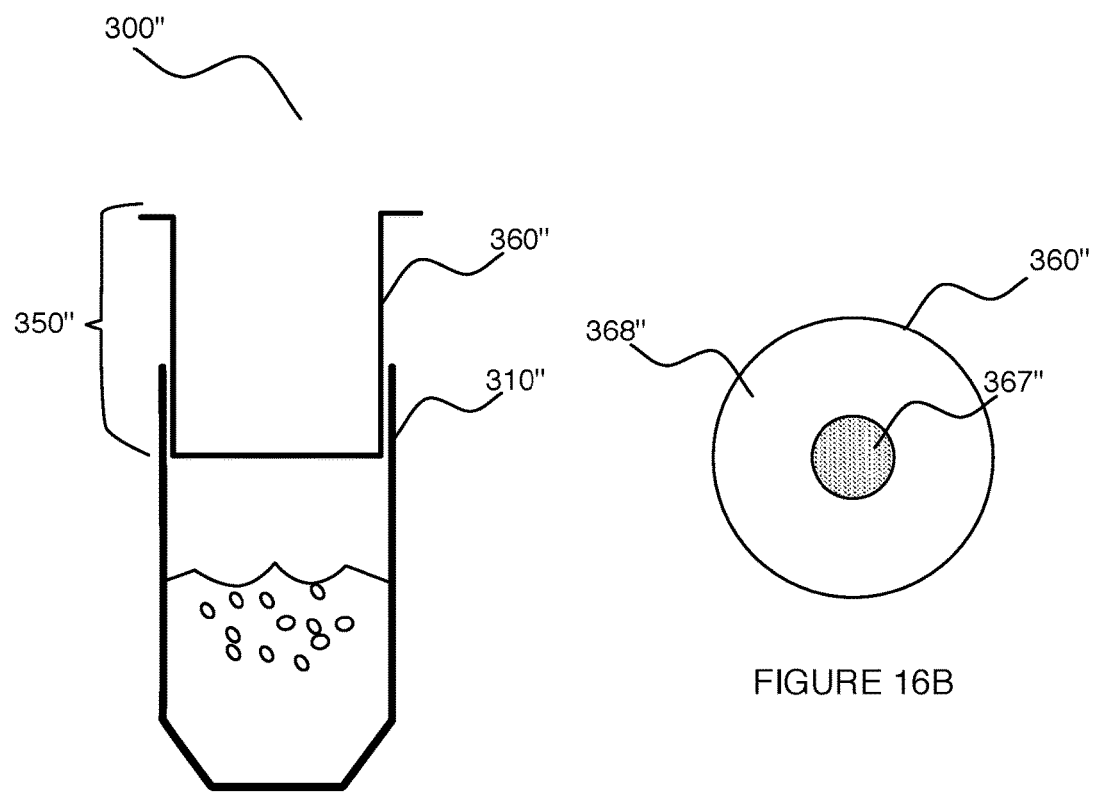

In the first variation, the first portion 360' of the extraction apparatus 350' having the frustoconical surface 362' preferably interfaces with a surface of the sample fluid in a first configuration (e.g., a compressed configuration), as shown in FIG. 15B, such that the feeding region 363' receives fluid of the sample and enables feeding of the population of target-bound complexes toward the opening 364' due to buoyant separation. In the first configuration, the collection tube 372' is in position to receive the population of target-bound complexes as they float in an inferior-to-superior direction, as shown in FIG. 15C. Finally, uncoupling of the second portion 370' from the first portion 360' of the extraction apparatus 350', as shown in FIG. 15D, enables extraction of the population of target-bound complexes from the sample, by way of the collection tube 372' of the second portion 370' of the extraction apparatus 350'. In the first variation, the first portion 360' and the second portion 370' of the extraction apparatus 350' can be positioned together and/or separately with respect to the process chamber 310' of the process chamber 300'. Furthermore, in the first variation, the first portion 360' and the second portion 370' of the extraction apparatus 350' can be displaced relative to each other and/or relative to the process chamber 310' by any one or more of a: screw mechanism, a sliding mechanism, a ratcheting mechanism, a magnetic mechanism, and any other suitable mechanism. Furthermore, motion between components of the system 300' of the first variation can be limited to a specified range (e.g., with a tab), in association with phases of sample processing to extract the target constituent from the sample.

In variations of the first variation, the opening 364' of the feeding region 363' and the collection tube 372' preferably mate with each other in a complementary manner, and furthermore are flush with each other in order to provide a sufficient seal that prevents particles of the population of target-bound complexes from entering undesired portions of the process chamber 300'. As such, in a specific example where the feeding region 363' is associated with the inverted frustoconical surface 366', as shown in FIG. 15A, the collection tube 372' can be coupled to a second inverted frustoconical surface 376' that is complementary to the inverted frustoconical surface 366' coupled to the feeding region 363'. However, the first portion 360' and the second portion 370' can alternatively interact with each other in any other suitable manner. Additionally or alternatively, in variations of the first variation, the process chamber 310' can receive fluid (e.g., buffer, sample) through a port (e.g., within the process chamber 310' and/or the extraction apparatus 350', in order to facilitate delivery of the population of target-bound complexes toward the feeding region 363' and/or the collection tube 372'.

In an alternative variation of the first variation, the extraction apparatus 350' can omit a second portion 370', where buoyant particles are configured to be transmitted from the process chamber 310' into the inverted frustoconical surface 366' of the first portion 360' (according to one or more of the methods describe in Block S140 above), and extracted from the inverted frustoconical surface 366' (according to methods described above).

Furthermore, while frustoconical surfaces are described in relation to the extraction apparatuses 350, 350', variations of the extraction apparatus can alternatively define any other suitable surface (e.g., broadening surface, narrowing surface) configured to facilitate concentration and/or extraction of buoyant particles from the process chamber.

In a second variation, as shown in FIGS. 16A-16F, the system 300" includes a process chamber 310" defining a volume for retention of the sample, within which the target constituent(s) of the sample can be combined with a volume of buoyant substrates that enable isolation of the target constituent from the sample in the form of a population of target-bound complexes. In the second variation, the extraction apparatus 350' comprises a first portion 360" including a hydrophilic region 367" and a hydrophobic region 368" at a surface configured to interface with a surface of sample fluid within the sample containing chamber 310". In the second variation, the hydrophilic region 367" is surrounded by the hydrophobic region 368", in order to define an area at which the population of target-bound complexes can be retained for extraction from the sample containing chamber 310". The size of the hydrophilic region 367" in the second variation can further be adjusted or adjustable to provide an area sufficient in size to retain a desired portion of the population of target-bound complexes at the first portion 360" of the extraction apparatus 350". In the second variation, the hydrophilic region 367" can be located at an external surface of the first portion 360" that interfaces with fluid of the sample in the sample containing chamber 310", or can alternatively be located at an interior surface of the first portion 360", and accessible through an opening into the first portion 360" that also enables venting of the process chamber during extraction. Additionally or alternatively, the hydrophilic region 367" can be composed of the same material as the first portion 360" of the extraction apparatus 350", wherein a coating of hydrophobic material provides the hydrophobic region 368" and isolates the hydrophilic region 367" to a desired area of the extraction apparatus. Furthermore, the hydrophilic region 367" can comprise any suitable morphology (e.g., convex morphology, textured morphology) that enhances contact between the hydrophilic region 367" and fluid of the sample in the sample-containing chamber 310".

In the second variation, the first portion 360" of the extraction apparatus 350" preferably interfaces with a surface of the sample fluid in a first operation mode (e.g., a compressed configuration), as shown in FIG. 16D such that the hydrophilic region 367" interfaces with the population of target-bound complexes due to buoyant separation in the sample. Upon displacement of the first portion 360" of the extraction apparatus 350" away from the sample container 310" in a second operation mode, as shown in FIG. 16E, the population of target-bound complexes, coupled to the hydrophilic region 367" by adhesion forces, is extracted from the sample containing portion 310" of the process chamber 300". Finally, uncoupling of the first portion 360" from the process chamber 310", as shown in FIG. 16F, enables extraction of the population of target-bound complexes from the sample. In the second variation, the population of target-bound complexes can then be retrieved (e.g., by pipetting) from the hydrophilic region 367" of the first portion 360" of the extraction apparatus. Similar to the first variation of the process chamber 300', in the second variation, the first portion 360" of the extraction apparatus 350' can be displaced relative to the sample containing chamber 310" by any one or more of: a screw mechanism, a sliding mechanism, a ratcheting mechanism, a magnetic mechanism, and any other suitable mechanism. Furthermore, motion between components of the process chamber 300' of the first variation can be limited to a specified range (e.g., with a tab), in association with phases of sample processing to extract the target constituent from the sample.

Figure 17A:
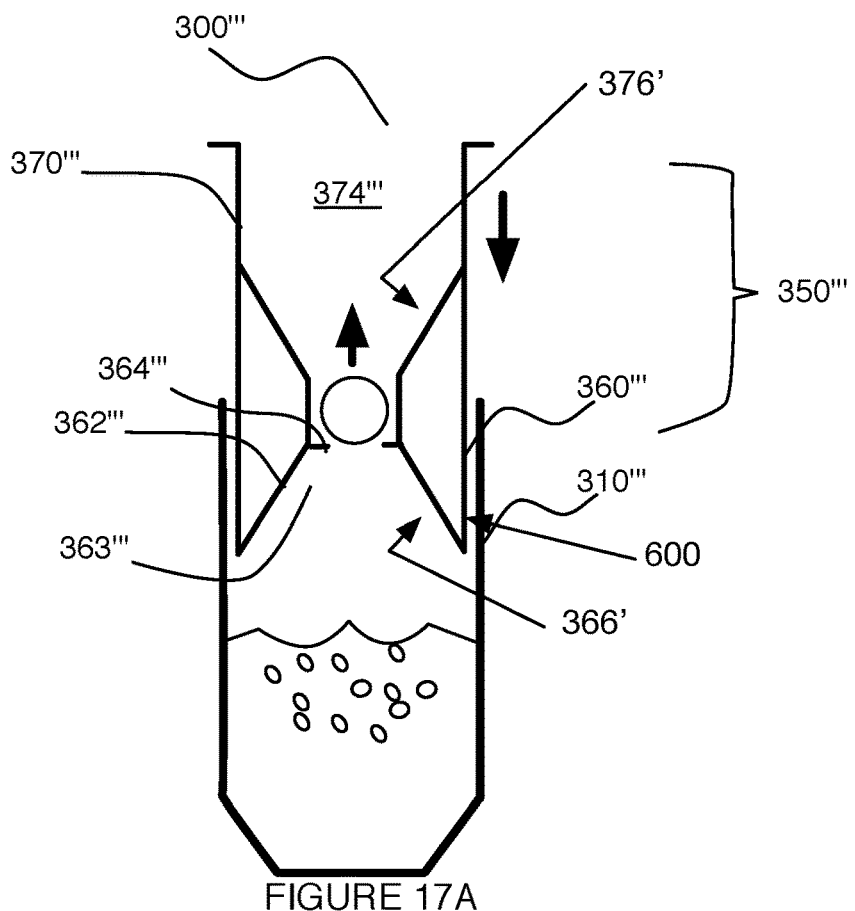
FIGS. 17A-17C depict a third variation of an embodiment of a system for buoyant separation of a target constituent of a sample.
Figure 17B:
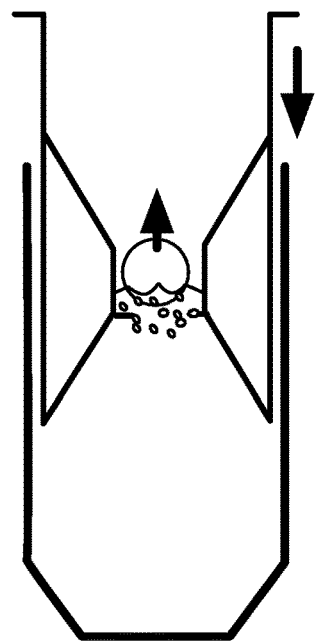
Figure 17C:
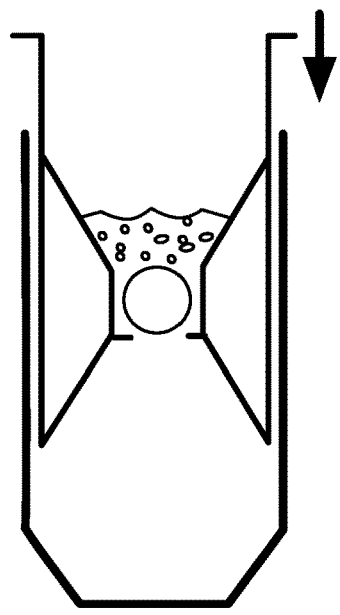

In a third variation, as shown in FIGS. 17A-17C the process chamber 300''' includes a sample containing chamber 310''' defining a volume for retention of the sample, within which the target constituent(s) of the sample can be combined with a volume of buoyant substrates that enable isolation of the target constituent from the sample in the form of a population of target-bound complexes. In the first variation, the extraction apparatus 350''' comprises a first portion 360''' including a frustoconical surface 362''' that defines a feeding region 363''' into an opening 364''' at a superior portion of the first portion 360'''; and a second portion 370''' comprising a valve 376''' (e.g., a ball valve, other valve, etc.) that interfaces with the opening 364''' in permitting controlled passage of the population of target-bound complexes into a collection region 378''' of the second portion 370'''. In the third variation, the second portion 370'''' includes a venting chamber 374'''' having an inverted frustoconical surface opposing the frustoconical surface 362''', configured to provide venting of the sample containing chamber 310'''' during relative displacement between the sample containing chamber and the extraction apparatus 350'''' for extraction of the population of target-bound complexes from the sample.

In the third variation, the first portion 360'''' of the extraction apparatus 350''' preferably interfaces with a surface of the sample fluid in a first configuration (e.g., a compressed configuration, prior to addition of fluid into the venting chamber 374''', etc.), as shown in FIG. 17B, such that the feeding region 363''' receives fluid of the sample and enables feeding of the population of target-bound complexes toward the opening 364''' due to buoyant separation. In the first configuration, the valve 376''' is displaced by fluid of the sample at a superior region of the process chamber 310''', thus allowing passage of the population of target-bound complexes, through the opening 364''' and into the venting chamber 374''' of the second portion 370''' of the extraction apparatus 350''', as shown in FIG. 17C. Finally, uncoupling of the extraction apparatus 350''' from the sample containing chamber 310''' enables extraction of the population of target-bound complexes from the sample. In the third variation, a specific volume of fluid (e.g., 100 μL, 200 μL) can be configured to pass into the second portion 370''' of the extraction apparatus 350''' upon transmission of the extraction apparatus 350''' into the first configuration within the process chamber (e.g., by linear displacement, by screwing the extraction apparatus and the process chamber relative to each other, etc.). The specific volume of fluid can be limited by a physical feature (e.g., notch) of the process chamber 300''' that physically stops fluid passage past the valve 376''' once the set volume of fluid has been obtained. However, the specific volume of fluid can be limited in any other suitable manner.

Similar to the first variation of the system 300, in the third variation, the first portion 360''' and the second portion 370''' of the extraction apparatus 350''' can be displaced relative to the sample containing chamber 310''' by any one or more of a: screw mechanism, a sliding mechanism, a ratcheting mechanism, a magnetic mechanism, and any other suitable mechanism. Furthermore, motion between components of the system 300''' of the first variation can be limited to a specified range (e.g., with a tab), in association with phases of sample processing to extract the target constituent from the sample. The system 300 can, however, comprise any suitable combination of the above variations and/or any other suitable process chamber for processing a sample and enabling extraction of a target constituent from the sample.

As such, the process chamber systems 200, 300 are preferably configured to perform at least a portion of the method 100 described in Section 1 above; however, the process chamber 200 can additionally or alternatively be configured to perform any other suitable method.

2.1 System—Alternative Variations

Figure 18A:
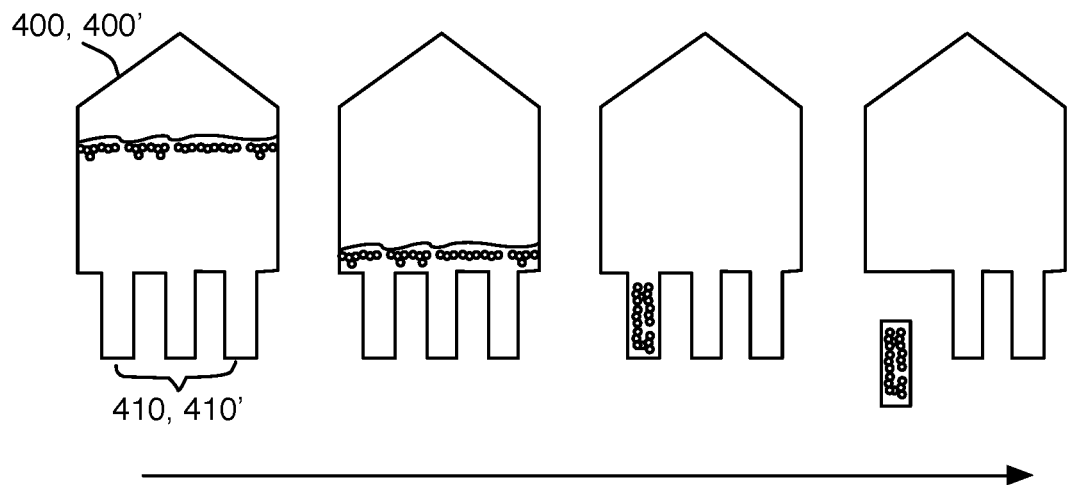
FIGS. 18A-18B depict a first alternative embodiment of a system for buoyant separation of a target constituent of a sample.
Figure 18B:
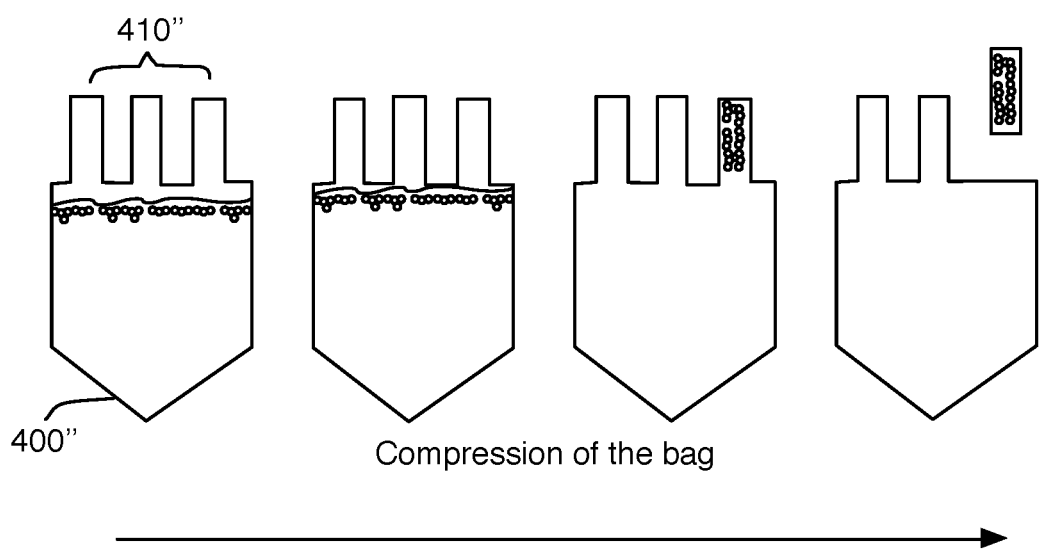

Alternative variations of the process chambers 200, 300 can, however, comprise any other suitable container (e.g., fluid receiving and/or distributing bag). For instance, in one variation aspects of the separation and/or extraction elements of the systems described above can be incorporated into a bag-type form factor (e.g., blood transfusion bag, leukopheresis bag, cell collection bag, etc.), where generating a population of target-bound complexes is performed, and the bag-type form factor facilitates separation and/or extraction of the population of target-bound complexes from a sample volume. In one such variation, as shown in FIGS. 18A and 18B, the bag 400 can include a set of stems 410 incorporated into the bag, that function to enable accessing of the bag for filling and emptying of contents of the bag 400. The stems 410 can additionally or alternatively function to facilitate testing of a sample (e.g., blood type crossmatching, etc.). In operation, the set of stems 410 can thus allow buoyant particles to be received into the bag 400, to interact with and bind to sample constituents of interest, and then to be separated, for instance, using a sealing mechanism (e.g., heat sealing mechanism) to seal portions of the bag 400 containing the buoyant particles from portions of the bag 400 that are substantially void of the buoyant particles.

In a first variation, as shown in FIG. 18A, the bag 400' can include a set of inferiorly located stems 410', such that draining of the bag 400' through one or more of the stems 410' causes a population of target-bound complexes within the bag to enter the stems 410', with a small amount of sample fluid, for extraction. Additionally or alternatively, in the first variation, one or more stems 410' of the bag 400' can be sealed off and/or removed from the bag 400', thereby enabling extraction of the population of target-bound complexes from the bulk sample.

In a second variation, as shown in FIG. 18B, the bag 400" can include a set of superiorly located stems 410", such that delivery of the population of target-bound complexes into the stems 410" (e.g., through compression of the bag, through buoyant forces, etc.) allows the population of target-bound complexes to be separated from the bulk sample volume in the bag 400". Additionally or alternatively, in the second variation, one or more stems 410" of the bag 400' can be sealed off and/or removed from the bag 400", thereby enabling extraction of the population of target-bound complexes from the bulk sample.

Figure 19A:
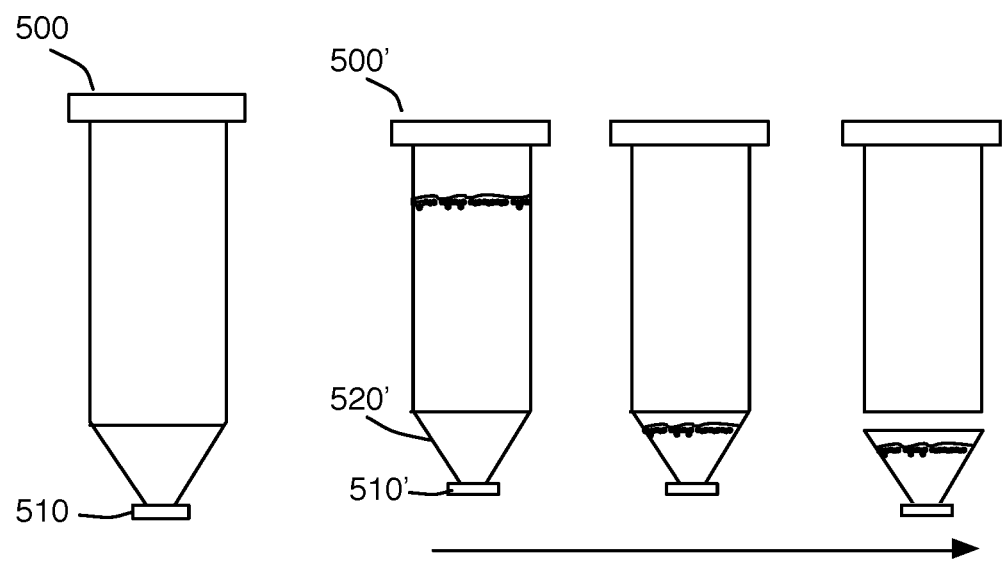
FIGS. 19A-19B depict a second alternative embodiment of a system for buoyant separation of a target constituent of a sample.

In still alternative embodiments, a process chamber 500, as shown in FIG. 19A, can include an outlet 510, wherein the outlet 510 can include one or more of: a puncturable diaphragm, a luer lock, a valve, and/or any other suitable outlet. The outlet can thus allow sample fluid and/or non-buoyant particles to be removed from the process chamber 500, without disturbing a region of separated buoyant particles. In variations of these alternative embodiments, the outlet 510 can thus facilitate one or more of: negative separation (e.g., to remove non-target constituents from the sample) and positive separation (e.g., to remove target constituents from the sample). Additionally or alternatively, the process chamber 500 and/or outlet 510 can facilitate performance of chemistry on buoyant particles (e.g., in a two-phase solvent system). Additionally or alternatively, the process chamber 500 and/or outlet 510 can facilitate removal of compromised buoyant particles (e.g., broken buoyant particles) from the bulk sample volume. However, the chamber 500 and/or outlet 510 can facilitate any other suitable operation in relation to the population of target-bound complexes.

In one variation, the process chamber 500' can include an inferiorly located outlet 510', such that draining of the process chamber 500' through the outlet 510' causes a population of target-bound complexes within the process chamber 500' to enter an inferior region of the process chamber 500' (in the orientation shown in FIG. 19A), with a small amount of sample fluid, for extraction. Additionally or alternatively, in the first variation, the inferior region 520' of the process chamber 500' can be configured to separate from the remainder of the process chamber 500', as shown in FIG. 19A, thereby enabling extraction of the population of target-bound complexes from the bulk sample.

Figure 19B:
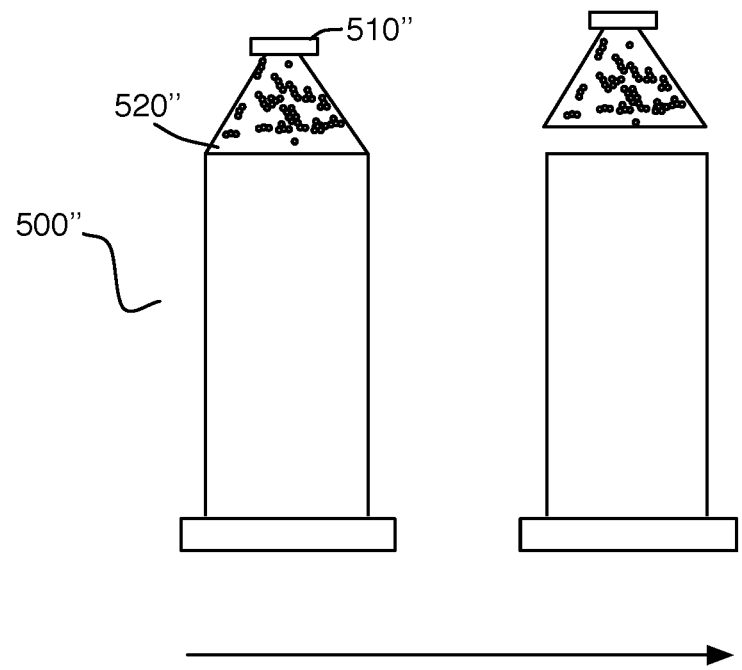

In an alternative variation, as shown in FIG. 19B, the process chamber 500" can include a superiorly located outlet 510", wherein delivery of the population of target-bound complexes into a superior region 520" of the process chamber 500' (e.g., through buoyant forces, etc.) allows the population of target-bound complexes to be separated from the bulk sample volume in the process chamber 500". Additionally or alternatively, in the second variation, the superior region 520" of the process chamber 500" can be sealed off and/or removed from the remainder of the process chamber 500", thereby enabling extraction of the population of target-bound complexes from the bulk sample. Additionally or alternatively, the process chamber 500" of this variation can be inverted, non-buoyant components of the sample can be drained from outlet 510", and then the process chamber 500" can then be reverted to a non-inverted orientation, whereby the population of target-bound complexes remains in the superior region 520" of the process chamber 500" due to surface tension between fluid coupled to the population of target-bound complexes and the wall of the superior region 520" of the process chamber. The superior region 520" of the process chamber 500" can then be sealed off and/or removed from the remainder of the process chamber 500", thereby enabling extraction of the population of target-bound complexes from the bulk sample.

Additionally or alternatively, variations of the process chambers 200, 300 can be composed of or otherwise include metallic regions (e.g., magnetic regions, ferromagnetic regions) configured to facilitate magnetic separation of the target constituent(s) of the sample according to methods described in Section 1 above. For instance, magnetic/ferromagnetic regions can facilitate formation of stray fields and/or directed magnetic fields that enable magnetic separation of sample components in addition to or in alternative to buoyancy-based separation methods.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The method 100 and/or system 200 of the preferred embodiment can be embodied and/or implemented at least in part as machine configured to receive a computer-readable medium storing computer-readable instructions. The instructions are preferably executed by computer-executable components preferably integrated with the system and one or more portions of the processor and/or analysis engine. The computer-readable medium can be stored in the cloud and/or on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A system for buoyant separation of a target constituent of a sample comprising:
   a process chamber including:
      a closed end and an openable end opposing the closed end, the process chamber configured to hold the sample having the target constituent and facilitate binding of the target constituent to a set of substrates to produce a set of buoyant target-bound complexes; and
   a target constituent extractor including:
      a frustoconical surface for transmission into the openable end of the process chamber, the frustoconical surface defining a base region having a first width and a concentration region having a second width, narrower than the first width, in opposition to the base region, wherein the frustoconical surface defines a volume configured to concentrate the set of buoyant target-bound complexes at the concentration region of the frustoconical surface;
      an extraction zone having an inverted frustoconical surface, in communication with the concentration region of the frustoconical surface by a channel that transmits the set of buoyant target-bound complexes into the extraction zone, for removal of the set of buoyant target-bound complexes from the concentration region; and
      a separate extraction component defining a second inverted frustoconical surface that is complementary to the inverted frustoconical surface, wherein a narrow end of the second inverted frustoconical surface is connected to a collection tube that, during operation, is 1) transmitted into the channel of the target constituent extractor and 2) receives the set of buoyant target-bound complexes from the concentration region.

2. The system of claim 1, wherein a peripheral region of the target constituent extractor includes a set of threads configured to engage a complementary set of threads of the process chamber, wherein, in a first operation mode, rotation of the target constituent extractor relative to the process chamber brings the frustoconical surface of the target constituent extractor into communication with fluid of the sample.

3. The system of claim 1, wherein the target constituent extractor is configured to be concentrically aligned with the process chamber, wherein, in a first operation mode, translation of the target constituent extractor deeper into the process chamber brings the frustoconical surface of the target constituent extractor into communication with fluid of the sample.

4. The system of claim 1, wherein the frustoconical surface of the target constituent extractor is separated from the inverted frustoconical surface by a valve, wherein, during operation, motion of the target constituent extractor deeper into the process chamber transmits fluid of the sample, with the set of buoyant target-bound complexes past the valve and into a region defined by the inverted frustoconical surface.

5. The system of claim 4, wherein the valve is a ball valve.

6. The system of claim 1, wherein an inferior region of the process chamber includes an outlet, and wherein the inferior region of the process chamber is detachable from a remaining portion of the process chamber.

7. The system of claim 1, wherein a superior region of the process chamber includes an outlet, wherein the superior region of the process chamber is detachable from a remaining portion of the process chamber.

8. The system of claim 1, wherein a wall of the target constituent extractor comprises a textured surface, wherein the textured surfaced comprises a molded surface, configured to enhanced retention of the set of buoyant target-bound complexes at the textured surface during at least one phase of operation of the system.

* * * * *